(12) United States Patent
Walker

(10) Patent No.: US 12,419,804 B2
(45) Date of Patent: Sep. 23, 2025

(54) SYSTEMS AND METHODS OF MANAGING AND EVALUATING EMERGENCY MEDICAL PROCEDURES

(71) Applicant: Physio-Control, Inc., Redmond, WA (US)

(72) Inventor: Robert G. Walker, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 16/862,451

(22) Filed: Apr. 29, 2020

(65) Prior Publication Data

US 2020/0253820 A1 Aug. 13, 2020

Related U.S. Application Data

(63) Continuation-in-part of application No. 16/478,817, filed as application No. PCT/US2018/014565 on Jan. 19, 2018.

(Continued)

(51) Int. Cl.
*A61B 5/08* (2006.01)
*A61B 5/00* (2006.01)
(Continued)

(52) U.S. Cl.
CPC ......... *A61H 31/005* (2013.01); *A61B 5/0816* (2013.01); *A61B 5/0836* (2013.01);
(Continued)

(58) Field of Classification Search
CPC .. A61H 31/005; A61H 31/006; A61H 31/007; A61H 2230/405; A61N 1/39044; A61B 5/0816; A61B 5/082; A61B 5/0836
See application file for complete search history.

(56) References Cited

U.S. PATENT DOCUMENTS 4,387,722 A * 6/1983 Kearns ................. A61B 5/0809
600/529
9,585,617 B2 * 3/2017 Babaeizadeh ....... A61M 16/021
(Continued)

FOREIGN PATENT DOCUMENTS

EP 2217141 A2 * 8/2010 ........... A61B 5/0816
JP 5395960 B2 * 1/2014 ........... H04R 25/453
WO WO-2012080920 A1 * 6/2012 ............. A61B 5/082

OTHER PUBLICATIONS

International Preliminary Report on Patentability dated Jul. 23, 2019, International App. No. PCT/US2018/014565, Filed Jan. 19, 2018.

(Continued)

*Primary Examiner* — Lynsey C Eiseman
*Assistant Examiner* — Jessica L Mullins
(74) *Attorney, Agent, or Firm* — Lee & Hayes, P.C.

(57) ABSTRACT

Systems, apparatuses, and methods directed to the collection and analysis of data related to a patient during an emergency advanced airway management process. The collected data may be obtained using various types of sensors, with the data collection process being managed or coordinated by a suitable system, such as a combination monitor-defibrillator. The monitor-defibrillator (alone or in combination with other system elements, such as a wired or wireless communications capability, a processor, data storage, etc.) may include a capability to process some or all of the acquired data, and in response indicate to a user when some of the collected data may be unreliable.

18 Claims, 10 Drawing Sheets

Related U.S. Application Data

(60) Provisional application No. 62/448,934, filed on Jan. 20, 2017.

(51) Int. Cl.
  *A61B 5/083* (2006.01)
  *A61H 31/00* (2006.01)
  *A61N 1/39* (2006.01)

(52) U.S. Cl.
  CPC ........ *A61B 5/6801* (2013.01); *A61N 1/39044* (2017.08); *A61H 2201/10* (2013.01); *A61H 2230/405* (2013.01); *A61H 2230/425* (2013.01)

(56) References Cited

U.S. PATENT DOCUMENTS

| | | | |
|---|---|---|---|
| 11,147,507 B2 | 10/2021 | Ronen et al. | |
| 2004/0122476 A1 | 6/2004 | Wung | |
| 2008/0215102 A1* | 9/2008 | Myklebust | A61H 31/005 607/6 |
| 2010/0174161 A1* | 7/2010 | Lynn | A61B 5/002 600/323 |
| 2011/0040713 A1* | 2/2011 | Colman | A61B 5/7264 706/16 |
| 2012/0137249 A1 | 5/2012 | Milne et al. | |
| 2013/0289364 A1* | 10/2013 | Colman | A61B 10/00 600/301 |
| 2013/0324873 A1* | 12/2013 | Babaeizadeh | A61B 5/4848 600/532 |
| 2014/0330155 A1 | 11/2014 | Koninklijke | |
| 2015/0182712 A1 | 7/2015 | Kelly et al. | |
| 2015/0265217 A1* | 9/2015 | Penders | A61B 5/681 600/300 |
| 2016/0058286 A1 | 3/2016 | Joshua et al. | |
| 2016/0287170 A1* | 10/2016 | Ronen | A61B 5/7235 |
| 2018/0182475 A1 | 6/2018 | Cossler et al. | |
| 2019/0216390 A1 | 7/2019 | Tang et al. | |
| 2020/0170513 A1 | 6/2020 | Walker | |
| 2021/0251501 A1* | 8/2021 | Moon | A61B 5/6826 |
| 2023/0364366 A1 | 11/2023 | Walker | |

OTHER PUBLICATIONS

International Search Report and Written Opinion dated Apr. 4, 2018, International App. No. PCT/US2018/014565, Filed Jan. 19, 2018.
Office Action for U.S. Appl. No. 16/478,817, dated Feb. 22, 2021, Walker, "Systems and Methods of Managing and Evaluating Airway Procedures", 22 pages.
Office Action for U.S. Appl. No. 16/478,817, dated Aug. 17, 2021, Walker, "Systems and Methods of Managing and Evaluating Airway Procedures", 18 Pages.
Office Action for U.S. Appl. No. 16/478,817, mailed on Mar. 27, 2023, Walker, "Systems and Methods of Managing and Evaluating Airway Procedures ", 12 pages.

* cited by examiner

Example Components of a Monitor - Defibrillator

Advanced Airway Management Report

| | | |
|---|---|---|
| Device Type: | LIFEPAK 15 | Header 402 |
| Power On: | 8/2/2015 7:01:19 AM | |
| Duration: | 0:49:57 | |
| Incident ID | 2015080207014600 | |

Physiological Measures 404

| % Time Monitored During Critical Time Interval | | |
|---|---|---|
| Pulse Oximetry: | 95% | Monitored Interval 406 |
| Waveform Capnography: | 50% | |
| Blood Pressure: | 40% | |
| ECG: | 88% | |

400

| Oxygenation Metrics During Critical Time Interval | | |
|---|---|---|
| SpO2 within normal limits (90%): | 68% | 0:10:02 / 0:15:00 |
| SpO2 < 90%: | 25% | 0:03:45 / 0:15:00 |
| SpO2 data not available | 7% | 0:01:13 / 0:15:00 |

Oxygenation Metrics 408

| Ventilation Metrics During Critical Time Interval | | |
|---|---|---|
| RR and EtCO2 within normal limits: | 50% | 0:05:00 / 0:10:00 |
| RR > 12 and EtCO2 < 35: | 24% | 0:02:24 / 0:10:00 |
| RR < 10 and EtCO2 > 45: | 15% | 0:01:30 / 0:10:00 |
| Capnography data not available: | 11% | 0:01:06 / 0:10:00 |

Ventilation Metrics 410

Vital Signs Excursions During Critical Time Interval

| Vital sign excursion | # episodes | Cumulative duration | Peak excursion | Longest interval |
|---|---|---|---|---|
| HR < 50 | --- | --- | --- | --- |
| HR > 120 | --- | --- | --- | --- |
| SpO2 < 80% | 1 | 3:15 | 68 | 3:15 |
| EtCO2 < 30 mmHg | 1 | 3:34 | 28 | 3:34 |
| EtCO2 > 50 mmHg | 1 | 4:30 | 57 | 4:30 |
| RR < 6 | --- | --- | --- | --- |
| RR > 20 | 2 | 4:08 | 24 | 2:51 |
| SBP < 80 mmHg | --- | --- | --- | --- |
| SBP > 160 mmHg | 1 | | 192/126 (168) | |

Vital signs Derangement metrics 412

| Breath Rate Distribution | | |
|---|---|---|
| > 30 / min | 0% | 0:00:00 |
| 20-30 / min | 4% | 0:00:24 |
| 15-20 / min | 13% | 0:01:18 |
| 12-15 / min | 35% | 0:03:30 |
| 10-12 / min | 46% | 0:04:36 |
| 8-10 / min | 2% | 0:00:12 |
| 4-8 / min | 0% | 0:00:00 |
| < 4 / min | 0% | 0:00:00 |

Breath rate Distribution 414

Figure 4(b)

SYSTEMS AND METHODS OF MANAGING AND EVALUATING EMERGENCY MEDICAL PROCEDURES

CROSS-REFERENCE TO RELATED APPLICATIONS

This application is a continuation-in-part of U.S. application Ser. No. 16/478,817, entitled "Systems and Methods of Managing and Evaluating Airway Procedures," filed on Jul. 17, 2019, which is a 371 filing of international patent application No. PCT/US2018/014565, entitled "Systems and Methods of Managing and Evaluating Airway Procedures," filed on Jan. 19, 2018, which claims the benefit of U.S. Provisional Patent Application Ser. No. 62/448,934, entitled "Post-Event Assessment of the Emergency Advanced Airway Management", filed on Jan. 20, 2017, the contents of which are incorporated by reference herein in their entirety.

BACKGROUND

Emergency procedures are a challenging, multifaceted, and often high-stress procedures, typically performed on patients in a serious and often life-threatening medical condition. Such emergency procedures can include cardiac arrest and emergency advanced airway management. One very common method of advanced airway management, particularly in emergency situations, is Rapid Sequence Intubation (RSI), which involves administration of specific medications to rapidly establish favorable conditions for attempting to place an advanced airway (such as a tracheal tube). The procedure is common to several different emergency and critical care settings, including prehospital care provided by Emergency Medical Services (EMS), as well as in-hospital care settings such as the Emergency Department (ED) and Intensive Care Unit (ICU). Clinical research has demonstrated that emergency procedures can be associated with significant risk of severe physiologic complications, due both to the underlying disease severity and physiologic instability of the patients, as well as to the quality with which the procedure is performed. Deviations from procedural best practices, suboptimal clinical decision-making, and care process errors that can threaten patient safety are all known to occur during some proportion of emergency airway management procedures.

Examples of physiologic derangements that may occur during emergent attempts to establish an advanced airway include the development of oxygen desaturation, hypotension, bradycardia, or cardiac arrest. Research reveals that medical providers of all levels sometimes experience delayed or failed recognition of such physiologic derangements as they are occurring, and may also experience other manifestations of diminished situational awareness in the stress of the moment, such as a failure to accurately perceive time intervals. The potential for harm from a sub-optimally performed procedure, combined with the care process and cognitive process challenges associated with the stressful situations in which the procedure may need to be performed (potentially contributing to procedural errors and increased risk to patient safety) highlight the need for improved systems and methods for monitoring, auditing, and debriefing the emergency advanced airway management care process, and for summarizing important details of the physiologic response of the patient during the critical phases of such procedures.

Given the complexity and criticality of emergency procedures, particularly when performed in the prehospital environment, such cases may be reviewed or audited after the fact in an attempt to assess care quality, protocol adherence, and the occurrence of adverse events, as well as to attempt to identify quality improvement needs and opportunities. However, currently such reviews/audits are typically focused on review of text documentation captured in the patient care record, which is often documented by the providers that performed the procedure, at some time point after the procedure is complete, and at least partially based on the provider's recollection of what happened during the procedure. This documentation typically includes only sporadic and often questionably-accurate physiologic monitoring values, and by definition does not include any details that the documenting provider was not aware of as the event transpired. It is known from the published literature that chart documentation of critical care procedures, such as rapid sequence intubation, under-reports the incidence of procedural and physiologic complications, and inaccurately captures important details such as time intervals and the magnitude of physiologic derangements associated with the procedure. These inaccuracies in the data collected and its interpretation may prevent recognition of serious errors in the performance of the procedure (or in the performance of immediate post-procedure patient care), and may also preclude identification of important opportunities for improvement of patient care at the level of both the individual provider and the medical system (e.g. EMS agency or hospital department) within which the provider works.

Physiologic monitors used during emergency care procedures are capable of recording and making available electronic physiologic monitoring data for transmission, download, or incorporation into the patient care record. Vital signs and related physiologic measurements (e.g. heart rate, blood pressure, oxygen saturation, respiratory rate, end-tidal carbon dioxide) are a prominent component of such electronic data. The accuracy of these physiologic measurements can sometimes be compromised by certain characteristics of the physiologic waveforms and physiologic sensor data from which the measurements are derived. These characteristics may variously be described as "artifacts", "abnormalities", or "features," and these terms are used interchangeably throughout the disclosure. While the presence of such characteristics is usually discernable in real time to users of physiologic monitors via the monitor's display of physiologic waveforms (e.g. ECG, pulse-oximetry photoplethysmograph, capnography carbon dioxide waveform, etc), the presence of such characteristics—and in turn a user's awareness of potential consequent inaccuracies in the derived vital signs and physiologic measurements—is commonly unknown to post-event users (e.g. users of patient care records, quality assurance or quality improvement reports, etc) because the physiologic measurements are no longer presented with or accompanied by the physiologic waveforms that exhibit such characteristics. This can lead to confusion and errors in interpretation of these physiologic measurements by post-event users of such data.

What is desired are improved systems and methods for real time, near real time, and post-event assessment of an emergency medical care process to provide more detailed, accurate, and actionable insights that may be used to further the quality assurance and quality improvement needs of emergency medical personnel and care delivery systems. The following discloses various embodiments for such improved systems and methods, both individually and collectively.

BRIEF DESCRIPTION OF THE DRAWINGS

Embodiments of the disclosure in accordance with the present disclosure will be described with reference to the drawings, in which:

FIGS. 4(a) and 4(b) are examples of aspects or portions of a summary report or display that may be generated in whole or in part by an embodiment of the systems and methods described herein;

Note that the same numbers are used throughout the disclosure and figures to reference like components and features.

SUMMARY OF EMBODIMENTS

Figure 1:
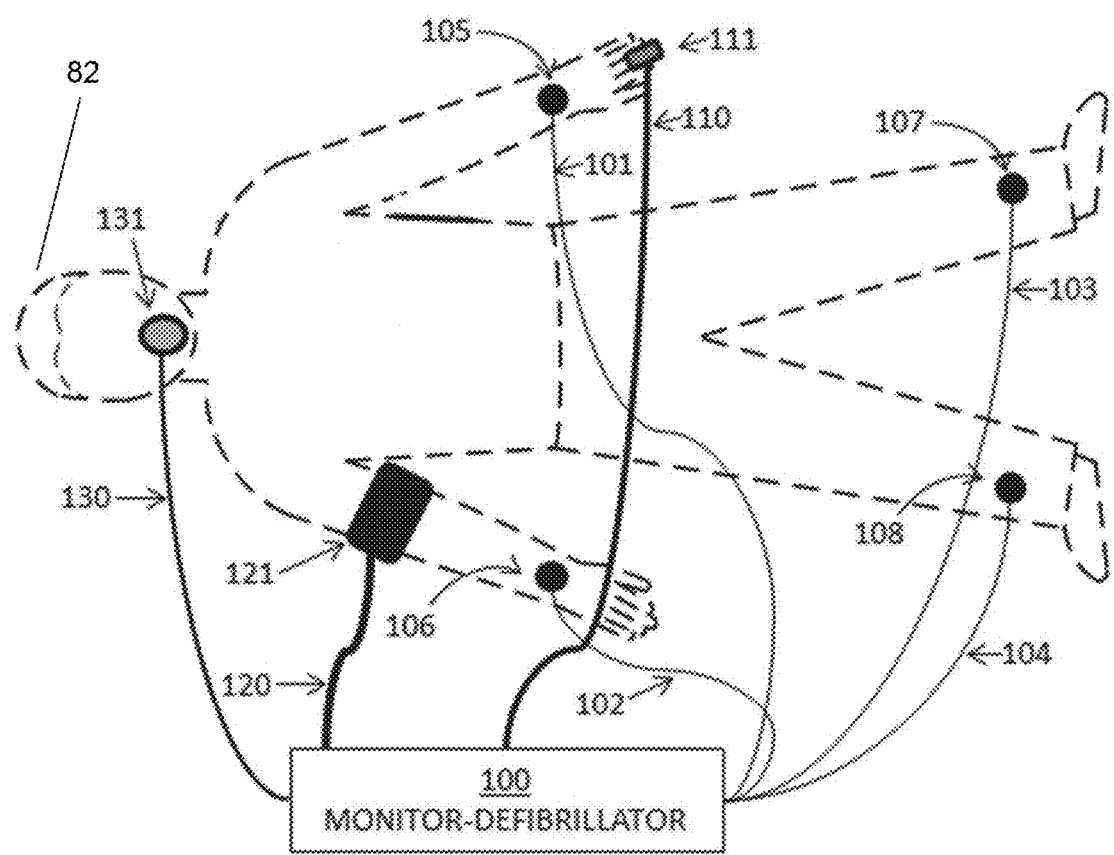
FIG. 1 is a diagram of a scene where a monitor-defibrillator is used to monitor multiple physiologic parameters (i.e., it is a multi-parameter monitor-defibrillator) of a patient undergoing an emergency advanced airway management procedure, and provides a possible context for use of an embodiment of the system and methods described herein.

Embodiments of the disclosure may include a device for evaluating measured carbon dioxide ($CO_2$) content in an exhaled breath, having one or more of the following features: an input configured to receive the measured $CO_2$ content; a processor configured to determine whether the measured $CO_2$ content includes artifacts; and a user interface configured to indicate a presence of at least one artifact when determined by the processor.

In some embodiments, the processor is further configured to determine a characteristic of the artifact and the user interface is configured to indicate the characteristic and/or generate a measurement based on the measured $CO_2$ content. The user interface may be configured to indicate the presence of the at least on artifact by indicating a likelihood that the measurement is unreliable when the measured $CO_2$ content includes artifacts. And in some embodiments, the measurement includes at least one of an end tidal $CO_2$ value or a respiratory rate.

Embodiments of the disclosure may include a device for evaluating measured carbon dioxide ($CO_2$) content in an exhaled breath, having one or more of the following features: an input configured to receive the measured $CO_2$ content; a processor configured to determine whether the measured $CO_2$ content includes chest compression induced artifacts; and a user interface configured to indicate a presence of at least one chest compression induced artifact when determined by the processor.

In some embodiments, the processor is further configured to determine a characteristic of the chest compression induced artifact and the user interface is configured to indicate the characteristic. The characteristic may be a magnitude of each chest-compression induced oscillation in the chest compression induced artifact or a proportion of a total interval the chest-compression induced artifact is present. The processor may also determine a respiratory/ventilation cycle and the characteristic can include a proportion of the respiratory/ventilation cycle in which the chest compression induced artifact occurred. The chest compression induced artifact may only be included in the total interval if a magnitude of the chest compression induced artifact is equal to or greater than a threshold.

Embodiments of the disclosure also include a method or operation for evaluating measured carbon dioxide ($CO_2$) content in an exhaled breath, having one or more of the following features: receiving the measured $CO_2$ content; determining whether the measured $CO_2$ content includes artifacts; and indicating a presence of at least one artifact when an artifact is determined to be present in the measured $CO_2$ content. The method may also include generating a measurement based on the measured $CO_2$ content, wherein indicating the presence of at least one artifact includes indicating a likelihood that the measurement is unreliable when the measured $CO_2$ content includes artifacts. The measurement may include at least one of an end tidal $CO_2$ value or a respiratory rate. Both the measurement and the likelihood the measurement is accurate may be displayed concurrently in some embodiments. The method or operation may also include determining a characteristic of the at least one artifact and indicating the characteristic on the display.

Embodiments of the disclosure may also include a device for evaluating measured carbon dioxide ($CO_2$) content in an exhaled breath, having one or more of the following features: an input configured to receive the measured $CO_2$ content; a processor configured to determine whether the measured $CO_2$ content data includes chest compression induced artifacts, and generate an end tidal $CO_2$ value based on the measured $CO_2$ content; and a user interface configured to indicate a likelihood that the end tidal $CO_2$ value is unreliable when the measured $CO_2$ content includes the chest compression induced artifacts.

The likelihood that the end tidal $CO_2$ value is unreliable may include a text alert message displayed concurrently with the end tidal $CO_2$ value. Additionally or alternatively, the likelihood that the end tidal $CO_2$ value is unreliable includes highlighting an affected portion of the end tidal $CO_2$ values. The processors may be further configured to omit from post-event data review the measured $CO_2$ content that includes the chest compression induced artifacts, or to include such content but visually identify it as containing chest compression induced artifacts.

Embodiments of the disclosure may also include a device for evaluating measured carbon dioxide ($CO_2$) content in an exhaled breath, having one or more of the following features: an input configured to receive the measured $CO_2$ content; a processor configured to determine whether the measured $CO_2$ content includes artifacts, and generate a measurement based on the measured $CO_2$ content; and a user interface configured to indicate a likelihood that the measurement is unreliable when the measured $CO_2$ content includes artifacts. The measurement may include at least one of an end tidal $CO_2$ value or a respiratory rate. The user interface can be configured to concurrently display the measurement and the likelihood the measurement is accurate.

In some embodiments, the processor is further configured to determine a characteristic of the artifacts and the user interface is figured to indicate the characteristic. The characteristic can include a value representing the artifact and/or a proportion of a total interval the artifact is present. The processor can also be further configured to determine a respiratory/ventilation cycle and the characteristic includes a proportion of the respiratory/ventilation cycle in which the artifact occurred. The artifact can be included in the total interval if a magnitude of the artifact is equal to or greater than a threshold.

Embodiments of the disclosure can also include a method for evaluating measured carbon dioxide ($CO_2$) content in an exhaled breath, having one or more of the following features: receiving the measured $CO_2$ content; determining whether the measured $CO_2$ content includes chest compression induced artifacts; and indicating a presence of at least one chest compression induced artifact when a chest compression induced artifact is determined to be in the measured $CO_2$ content.

Embodiments of the disclosure can also include a method for evaluating measured carbon dioxide ($CO_2$) content in an exhaled breath, having one or more of the following features: receiving the measured $CO_2$ content; determining whether the measured $CO_2$ content includes chest compression induced artifacts; generating an end tidal $CO_2$ value based on the measured $CO_2$ content; and indicating a likelihood that the end tidal $CO_2$ value is unreliable when the measured $CO_2$ content includes the chest compression induced artifacts.

Any of the devices above may be a monitor-defibrillator or a post-event review device. The processors of the devices may be a single processor, or may be a multi-core or multi-unit processor.

Detailed Description

Described herein are methods and systems for generating and using a post-event management report, incorporating specific Figures of Merit intended to better identify and quantify the quality with which an advanced procedure was performed, as well as the patient's physiologic status and response to the procedure. As mentioned, emergency advanced airway management is a challenging, multifaceted, and often high-stress procedure, typically performed on patients in a serious and often life-threatening medical condition. The potential for harm from a sub-optimally performed procedure, combined with the care process and cognitive process challenges associated with the stressful situations in which the procedure may need to be performed (potentially contributing to procedural errors and increased risk to patient safety), highlight the need for improved systems and methods for monitoring, auditing, and debriefing the emergency advanced airway management care process, and for summarizing important details of the physiologic response of the patient during the critical phases of such procedures.

In some embodiments, the systems, apparatuses, and methods disclosed herein are directed to the collection and analysis of data related to a patient during an emergency advanced airway management process. The collected data may be obtained using various types of sensors, with the data collection process being managed or coordinated by a suitable system, such as a combination monitor-defibrillator.

The monitor-defibrillator (alone or in combination with other system elements, such as a wired or wireless communications capability, a processor, data storage, etc.) may include a capability to process some or all of the acquired data, and in response to generate a summary report containing one or more figures-of-merit that may be of assistance in evaluating the airway management process. In some embodiments, the Figures of Merit (FOM) referred to or described herein may be considered: (1) the % of a time interval of specific and critical clinical significance where specific criteria (of either signals from one or more sensors, or parameters derived from those signals) are met, (2) a representation of the distribution of signal characteristics or parameter values within that time interval of specific and critical clinical significance, or (3) the minimum or maximum value, or maximum percent change, of a physiologic parameter measured during the time interval of specific and critical clinical significance.

In some embodiments, the systems, apparatuses, and methods disclosed herein are directed to the collection and analysis of data related to a cardiac arrest of a patient or other emergency procedure. The collected data may be obtained using various types of sensors, with the data collection process being managed or coordinated by a suitable system, such as a combination monitor-defibrillator. The monitor-defibrillator (alone or in combination with other system elements, such as a wired or wireless communications capability, a processor, data storage, etc.) may include a capability to process some or all of the acquired data, and in response alert a user that one or more of measured physical trend values may be unreliable due to artifacts present in the physiological data received.

In one or more embodiments, a summary report is disclosed herein that is generated at the end of a patient care event in which an emergency procedure was performed. In some cases, the care event includes an advanced airway procedure such as rapid sequence intubation (RSI) and positive pressure ventilation, performed on a patient not currently in cardiac arrest, and not receiving cardiopulmonary resuscitation (CPR). In some embodiments, the summary report graphically depicts physiologic trend data from multiple monitoring parameters (e.g. Heart Rate, Arterial Oxygen Saturation, Cerebral Oxygen Saturation, Respiration/Ventilation Rate, End-tidal $CO_2$, Blood Pressure, etc.), as recorded by a multi-parameter physiologic monitor, which may be a combined monitor-defibrillator.

In other embodiments, a summary report is disclosed herein that is generated at the end of a patient care event a patient is in cardiac arrest, and is receiving cardiopulmonary resuscitation (CPR). In some embodiments, the summary report graphically depicts physiologic trend data from multiple monitoring parameters (e.g. Heart Rate, Arterial Oxygen Saturation, Cerebral Oxygen Saturation, Respiration/Ventilation Rate, End-tidal $CO_2$, Blood Pressure, etc.), as recorded by a multi-parameter physiologic monitor, which may be a combined monitor-defibrillator.

As mentioned, given the complexity and criticality of emergency procedures, particularly when performed in the prehospital environment, such cases may be reviewed or audited after the fact in an attempt to assess care quality, protocol adherence, and the occurrence of adverse events, as well as to attempt to identify quality improvement needs and opportunities. Further, currently such reviews/audits are focused on review of text documentation captured in the patient care record, which is often documented by the providers that performed the procedure, at some time point after the procedure is complete, and at least partially based on the provider's recollection of what happened during the procedure. This documentation by definition does not include any details that the documenting provider was not aware of as the event transpired, even though such details may be of great significance in determining whether the procedure was performed optimally, and whether the patient's physiologic responses to the procedure were indicative of actual harm or "near miss" patient safety threats. These inaccuracies and omissions in the data collected and its interpretation may prevent recognition of errors in the emergency advanced airway management process, and may also preclude identification of important opportunities for improvement of patient care at the level of both the individual provider and the medical system (e.g. EMS agency or hospital department) within which the provider on other patients or in post-procedure patient care.

Thus, in some embodiments, the systems, apparatuses, and methods disclosed herein are directed to the improvement of emergency treatment for a patient. Further, the disclosed embodiments are also directed to the auditing review, risk management, continuum of care, training and/or evaluation of emergency rescuers. In this regard, the evaluation of the sensor data for one or for an aggregation of patients may indicate that a change in the care process is needed or would be an improvement.

In some embodiments, the systems, apparatuses, and methods disclosed herein are directed to the collection and analysis of data related to a patient during an emergency advanced airway management process. The collected data may be obtained using various types of sensors, with the data collection process being managed or coordinated by a suitable system, such as a combination monitor-defibrillator. The monitor-defibrillator (alone or in combination with other system elements, such as a wired or wireless communications capability, a processor, data storage, etc.) may include a capability to process some or all of the acquired data, and in response to generate a summary report containing one or more figures-of-merit that may be of assistance in evaluating the airway management process. In general, the Figures of Merit (FOM) referred to or described herein may be considered: (1) the % of a time interval of specific and critical clinical significance where specific criteria (of either signals from one or more sensors, or parameters derived from those signals) are met, (2) a representation of the distribution of signal characteristics or parameter values within that time interval of specific and critical clinical significance or (3) the minimum or maximum value, or the maximum percent change, of a physiologic parameter measured during the time interval of specific and critical clinical significance.

In one or more embodiments, the report depicts trend data for the entire interval that data are available, and for any and all of the monitored parameters. Typically for patient care events where an emergency advanced airway management procedure is performed, monitoring is performed (and thus recorded monitoring data are available) for all or a substantial portion of the time that a medical provider or team is attending to the patient, whereas the emergency airway management procedure itself (and thus its inherent physiologic hazards and the associated quality-of-care insights) only occupies a portion of the entire interval from which physiologic monitoring data are available. Thus in some embodiments, the report also includes one or more figures-of-merit (FOM), derived from one (or more) of the monitored parameters, and measured over a specific subset of the overall interval that the constituent parameter(s) contributing to the figure-of-merit were monitored. This sub-interval represents the portion of patient care process associated specifically with one or more stages of the emergency airway management procedure.

Options for determining/selecting the pertinent sub-interval include, but are not limited to, a software process automatically determining a relevant sub-interval or a user of the report software identifying one or more key time points from the process-of-care. In accordance with one or more rules, heuristics, or algorithms, a software process may automatically determine this sub-interval via utilization of one or more time-stamped process-of-care event markers recorded automatically by the monitor (or another communicatively-coupled device), or documented by a provider using a feature (such as an event marking feature) on the monitor (or on another communicatively-coupled electronic device). Examples of possible communicatively-coupled electronic devices include an electronic patient care reporting tablet, a smartphone app, a video laryngoscope, a ventilator, an IV infusion pump, and a computer-assisted dispatch system that tracks the status and/or location of an EMS response vehicle such as an ambulance. Alternately, a user of the report software may identify and demark this sub-interval within the report software based upon pertinent information available to them during the post-event review of the patient care event. Examples of such pertinent information may be a paper or electronic copy of a patient care report, or audio or video recordings of the patient care event which can be reviewed to determine the key process of care time points.

The time point(s) used to define the sub-interval generally consist of discrete events that occur a single time during the process of managing a patient's airway within a given patient encounter, and thus represent "boundaries" that distinguish critical stages of the emergency airway management process and that separate these stages from other portions of the overall patient care event, including portions not directly associated with the emergency advanced airway management procedure. Examples of such time points, in the context of an emergency advanced airway management procedure such as RSI, include, but are not limited to: induction of anesthesia (i.e. administration of the anesthesia medications), initiation of laryngoscopy, successful placement of the advanced airway, and hand-off of the patient to the next care location and/or team (e.g. EMS hand-off of the patient to the ED, or ED hand-off of the patient to the ICU). Note thus that these time points are not arbitrarily specified by a user, but rather are tied to specific key events within an emergency airway management process. Note also that with respect to providing insight into the quality of the airway management process, information (e.g., certain vital signs values, or derived metrics) may be of no particular significance on one side of the time point "boundary", and of high (or relatively higher) significance on the other side of the "boundary". Note also that the reliability, accuracy, or interpretation of the measured parameters may vary across the boundary due to one or more of several possible reasons; these reasons may include sensor or measurement device operating conditions, patient condition, relevance of parameter to patient condition, etc.

In some embodiments, the systems and methods described herein may be used to collect data prior to, during, and in some cases after the performance of an emergency advanced airway management procedure on a patient. In a typical scenario (although not in all cases where an embodiment may be used), a patient is being treated using a multi-parameter monitor-defibrillator of the type described with reference to FIG. 1. The monitor-defibrillator or other source of data collection relating to the patient's physiologic parameters (such as pulse rate, oxygenation, etc.) contains connections to sensors that monitor the patient, and may include data processing capabilities to enable the processing of sensor data and the presentation of the data and/or the result of processing the data to a medical professional. Note that the collected data may be transferred or otherwise provided to a remote computer, data processing platform or other device or apparatus for the processing of the data and the generation and presentation of the Airway Management Report described herein.

In some embodiments, the figures-of-merit (FOM), derived from one (or more) of the monitored parameters, and measured over a specific subset of the overall interval that the constituent parameter(s) contributing to the figure-of-merit were monitored may be presented to a service provider during the provision of a medical service. For example, in some embodiments, a ventilation abnormality index or hypoxemia dose index (both of which are described in greater detail herein) may be calculated or derived as a FOM and updated continuously or regularly during the provision of a medical service. This information may be used to provide a service provider with feedback regarding the patient condition or effectiveness of the medical service while the service is being provided. In response, the service provider may alter the care process, such as by introducing additional medication or performing a different procedure.

FIG. 1 is a diagram of a scene where a multi-parameter monitor-defibrillator, such as commonly utilized by EMS personnel, is used during the management of a person receiving an emergency advanced airway management procedure, such as RSI. FIG. 1 provides a possible context for use of an embodiment of the system and methods described herein. As shown in the figure, there is an illustration of a medical device 100 (such as a multi-parameter monitor-defibrillator, MPMD) use scene in which a patient is having multiple physiologic parameters (in this example, ECG, pulse oximetry, capnography, and non-invasive blood pressure) monitored by the medical device 100 (again, where the device may be a multi-parameter monitor-defibrillator). The person 82 is lying on his or her back, but in other examples the person could alternately be oriented in a seated or semi-reclined position. The person 82 could be a patient in a hospital, or in the prehospital environment. In one example, the person 82 is experiencing an acute medical emergency that meets clinical indications for an advanced airway management procedure such as RSI. Examples of commonly accepted indications for such a procedure are airway protection for a patient with decreased level of consciousness or other threat to airway patency, and respiratory failure with inability to oxygenate or ventilate adequately by less invasive means.

As shown in the figure, a portable multi-parameter monitor-defibrillator 100 has been brought close to the person 82. ECG electrodes 105-108 have been applied to the skin on each of the arms and legs of person 82, and ECG wires 101-104 connect those electrodes to the monitor-defibrillator 100, allowing the monitor-defibrillator 100 to monitor the person's ECG (electrocardiogram). Note that the number of ECG electrodes and associated wires utilized may vary, but typically will involve at least four ECG electrodes and associated wires. A pulse oximetry sensor 111 has been placed on a finger of person 82, and connected to the monitor-defibrillator via a cable 110, allowing pulse oximetry monitoring (monitoring of the oxygen saturation and pulse rate of person 82). Note that in other examples the pulse oximetry sensor could be placed on other parts of the body, such as the ear, forehead, nose, toe, etc. A non-invasive blood pressure (NIBP) cuff 121 has been attached to the arm of person 82, connected by tubing 120 to the monitor-defibrillator 100, allowing measurement of the blood pressure of person 82. Note that in other examples, the NIBP sensor may be of varying size and construction, and may be placed on other parts of the body, such as a wrist or finger. A capnography gas sampling adaptor 131 has been attached to the airway of person 82, connected by tubing 130 to the monitor-defibrillator 100, allowing measurement of capnography parameters such as end-tidal carbon dioxide concentration (EtCO2) along with breath rate or respiratory rate (RR).

EtCO2 is a physiologic measurement commonly monitored during emergency care of patients and it represents the maximum partial pressure, or maximum concentration, of CO2 measured in an exhaled breath of a patient over a certain interval of time. This maximum level is often measured from a fixed interval, which may be, for example, 20 seconds, of continuous CO2 waveform data prior to a time point the EtCO2 measurement is presented on a monitoring display and/or logged in a data logger. The EtCO2 measurement may be updated at a fixed interval with a new measurement generated at the fixed interval, such as every one or two seconds. Alternatively, in some embodiments, the maximum value is alternatively measured over an interval of a single breath cycle and updated with each new breath cycle. Regardless of which approach is used to define the EtCO2 measurement interval, instantaneous EtCO2 measurements resent a peak value measured in a preceding CO2 waveform segment of a certain short duration.

Note that in other examples the capnography gas sampling adaptor may instead be a capnography sensor, and the connecting tubing may instead be a connecting cable. In other words, capnography monitoring may be performed via either a "sidestream" or a "mainstream" approach; these two alternatives are familiar to those skilled in the art of capnography. Also the gas sampling adaptor or sensor may be attached in various ways to the patient's airway, depending on what airway device or management strategy is being utilized at a given time point during the patient care process. For example, the capnography adaptor/sensor could be attached between a manual resuscitation bag and a face mask, or between a manual resuscitation bag and a tracheal tube or supraglottic airway.

Note that the medical device 100 can be one of different types, each with a different set of features and capabilities. The set of capabilities of the device 100 is determined by planning who would use it, and the specific device capabilities those medical providers would be likely to require.

A first type of device 100 is generally called a defibrillator-monitor because it is typically formed as a single defibrillation unit in combination with a patient physiologic monitor. A defibrillator-monitor is sometimes called a monitor-defibrillator. A defibrillator-monitor is intended to be used in a pre-hospital or hospital setting, by persons in the medical professions, such as doctors, nurses, paramedics, emergency medical technicians, etc.

As a patient monitor, the device 100 has features additional to what is needed for operation as a defibrillator. These features can be for monitoring physiological indicators of a person in an emergency scenario. These physiological indicators are typically monitored as signals. For example, these signals can include a person's ECG (electrocardiogram) signal or impedance between two electrodes. Additionally, these signals can relate to the person's temperature, non-invasive blood pressure (NIBP), arterial oxygen saturation/ pulse oximetry (SpO2), the concentration or partial pressure of carbon dioxide in the respiratory gases (known as capnography), and so on. These signals can be further stored and/or transmitted as patient data.

A second type of device 100 could be a physiologic monitor without any defibrillation capability. Such a device is often called a multi-parameter monitor or just called a monitor, and provides features for monitoring physiologic indicators as described above.

Figure 3:
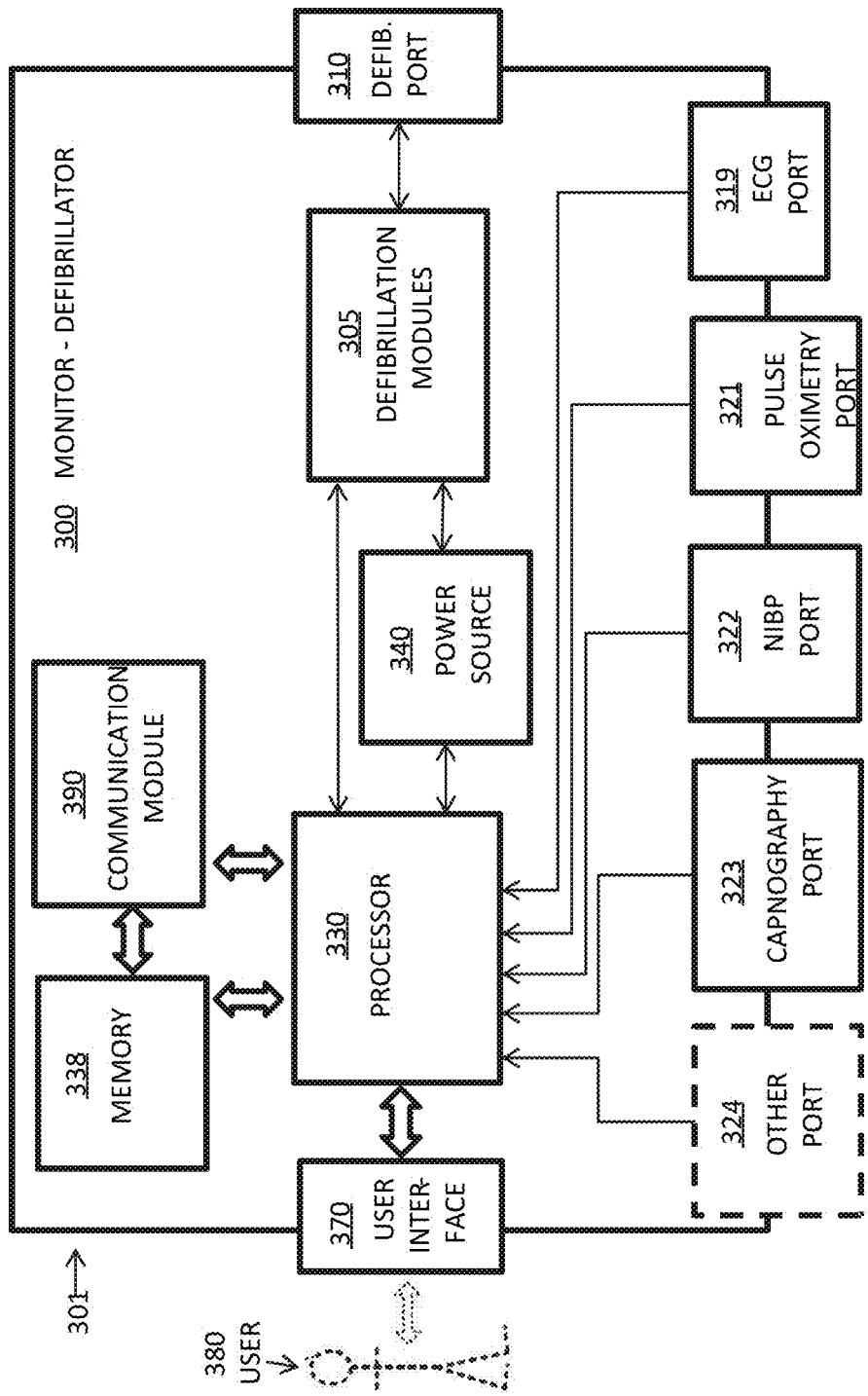
FIG. 3 is a functional block diagram showing example components of a multi-parameter monitor-defibrillator, such as the one shown in FIG. 1.

FIG. 3 is a functional block diagram showing example components of a monitor-defibrillator 300. These components can be, for example, in the monitor-defibrillator 100 of FIG. 1. Additionally, the components of FIG. 3 can be provided in a housing 301, which can also be known as a casing 301. The monitor-defibrillator 300 is intended for use by a user 380, who is a medical provider such as a paramedic, nurse, or doctor. The monitor-defibrillator 300 typically includes a defibrillation port 310, such as a socket in the housing 301. Defibrillation electrodes can be plugged into the defibrillation port 310 and attached to a patient, allowing delivery of defibrillation shocks or external pacing pulses to the patient. One or more defibrillation modules 305 within the monitor-defibrillator perform processes and functions well known to those skilled in the art—such as energy storage and energy discharge—associated with performing defibrillation and pacing.

The monitor-defibrillator 300 will typically have several additional ports for purposes of collecting physiologic signals and measurements from a patient. These ports may include an ECG port 319, into which are plugged ECG leads, such as elements 101-104 of FIG. 1, in order to sense one or more ECG signals from the patient. A pulse oximetry port 321 allows connection of a pulse oximetry cable and sensor, such as shown with elements 110 and 111 of FIG. 1, in order to measure SpO2 and collect associated pulse oximetry data from a patient. An NIBP port 322 allows connection of tubing and a cuff, such as shown with elements 120 and 121 of FIG. 1, in order to measure the blood pressure of a patient. A capnography port 323 allows connection tubing, or alternatively a cable and sensor, such as shown with elements 130 and 131 of FIG. 1, in order to sense carbon dioxide levels in the airway of a patient and measure capnography parameters such as EtCO2 and breath rate. One or more additional ports 324 may also be provided in the monitor-defibrillator, allowing collection of additional physiologic signals and measurements from a patient. Examples of such additional physiologic signals and measurements include, but are not limited to, invasive blood pressure, airway pressure, airway flow, ventilation tidal volume, regional tissue oxygen saturation, and oxygen levels in the airway of a patient. Note that some or all of the ports may be physical ports such as depicted in FIG. 3, or they may alternatively be "wireless ports", wherein the monitor-defibrillator receives physiologic signals and measurements from patient sensors via a wireless data streaming linkage.

The monitor-defibrillator 300 also typically includes a processor or processing element 330 (such as a central processing unit (CPU), controller, etc.) that may be implemented in a number of ways. Such ways include, by way of example and not limitation, digital and/or analog processors such as microprocessors and digital-signal processors (DSPs); controllers such as microcontrollers; computer-executable software being executed by a processor, apparatus or device; programmable circuits such as Field Programmable Gate Arrays (FPGAs), Field-Programmable Analog Arrays (FPAAs), Programmable Logic Devices (PLDs), Application Specific Integrated Circuits (ASICs), or any combination of one or more of these, etc.

The processor 330 can include a number of modules or elements, and may access a number of sets of software instructions that when executed, are used to implement particular functions, methods, processes, or operations. The set or sets of software instructions may be stored in a suitable non-transitory data storage medium, where non-transitory refers to a data or other form of storage medium other than a transitory waveform or similar medium. The processor receives information from various components or elements of the monitor-defibrillator, including from ports 310, 319, 321, 322, 323, and 324.

Monitor-defibrillator 300 optionally further includes a memory 338, which can work together with the processor 330. The memory 338 may be implemented in any number of ways. Such ways include, by way of example and not of limitation, nonvolatile memories (NVM), read-only memories (ROM), random access memories (RAM), any combination of these, and so on. The memory 338, if provided, can include programs or instruction sets to be executed by the processor 330, and so on. In addition, the memory 338 can store prompts for the user 380 and can store patient physiologic monitoring data, event data, and device status data, as needed.

The monitor-defibrillator 300 may also include a power source 340. To enable portability of the monitor-defibrillator 300, the power source 340 typically includes a battery. Such a battery can be implemented as a battery pack, which may be rechargeable or not. Sometimes, a combination is used, of rechargeable and non-rechargeable battery packs. Other embodiments of power source 340 can include AC power override that allows a rescuer to use AC power when such a source exists, but rely on the battery power if AC power is unavailable. In some embodiments, the power source 340 is controlled by the processor 330.

The monitor-defibrillator 300 further includes a user interface 370 for the user 380. For example, the interface 370 may include a screen to display physiologic monitoring waveforms and associated vital signs values, device status information, and data entry or device configuration windows, sub-displays, data entry fields, etc. The interface 370 may also include a speaker to issue voice prompts, alarms, audible alerts or otherwise audibly interact with the user and may additionally include various controls, such as pushbuttons, keyboards, and so on, as needed or desired.

The monitor-defibrillator 300 can optionally include other components. For example, a communication module 390 may be provided for communicating with other systems, networks, or devices. Such communication can be performed wirelessly (such as by WiFi or Bluetooth), via a wired connection, or by infrared communication, and so on. This way, data can be communicated, such as patient data, device usage and actions data, physiologic monitoring data, incident information, therapy attempted, CPR performance, and the like.

In general, the monitor-defibrillator 300 and/or associated components may include the ability to be networked with other devices, components, or systems used to monitor patient medical characteristics, provide patient-related data to medical professionals, generate graphs, images, or videos of a patient's measured characteristics, control data acquisition from sensors, and assist in diagnosing a patient's condition and applying the appropriate services or treatments. The "networking" may be the result of monitor-defibrillator 300 being capable of communications and/or data transfer with other devices, components, or systems over a wired and/or wireless network connection, using any suitable technology, mechanism, or protocols. For example, such technology, mechanism, or protocols may include (but are not limited to, or required to include) WiFi, Bluetooth, NFC, HTTP/TPC, etc. The systems or components that monitor-defibrillator 300 interacts with may include (but are not limited to, or required to include) other monitors, video laryngoscopes, ventilators, infusion pumps, electronic patient care documentation devices, printers, displays, communication devices, other processors, servers, etc.

Further, due to the ability to collect data from one or more sensors, various advanced data processing and analysis techniques may be used to process sensor data and to assist in diagnosing and treating a patient. For example, machine learning, statistical analysis, pattern matching, and other forms of data analysis may be used to derive useful information about a patient or their treatment from the collected data. In some cases, data collected from a set of patients or patient events may be used (typically in an anonymized, patient identification protected, or encrypted form) to evaluate the factors that are believed to be associated with a specific patient state or condition. For example, this may be useful in identifying previously unrecognized factors that are present when a patient undergoes a certain type of event or treatment.

In some embodiments, a monitor-defibrillator of the type described with reference to FIG. 1 or FIG. 3 is used to monitor a patient receiving prehospital assessment and care by EMS personnel. The EMS personnel begin monitoring the patient with, for example, ECG, pulse oximetry, and a capnography-sampling nasal cannula. At some subsequent point, the EMS personnel may determine that it is desirable to perform rapid sequence intubation (RSI) or other airway management procedure, and begin preparations to do so. At this point they begin using the non-invasive blood pressure monitoring function of the monitor-defibrillator, automatically cycling blood pressure measurements every few minutes. They then perform RSI, and upon placing the endotracheal tube, switch their capnography monitoring to use of a gas sampling adapter (or capnography sensor) placed on the end of the endotracheal tube. They then load the patient into the ambulance, transport the patient to a hospital, where they unload the patient from the ambulance and transfer care of the patient to the hospital's emergency department.

To perform a review or audit of the patient encounter, and specifically, the advanced airway management component of the patient encounter, an individual associated with the EMS agency, such as the EMS medical director, a clinical supervisor or preceptor, or the EMS personnel who performed the emergency airway management procedure themselves, would typically access a downloaded monitor-defibrillator data file using the post-event data review functions and capabilities of embodiments of the system and methods described herein. The monitor-defibrillator data file may contain various information including: patient physiologic waveforms and vital signs measurements, device status and usage information, event information captured automatically by the device or marked by the device user, information on therapy delivered, audio and video data captured during a patient care event, and data acquired from a separate communicatively-coupled device in use during the patient care event, such as a video laryngoscope, a point-of-care ultrasound system, and IV infusion pump, or a ventilator.

The monitor-defibrillator data file may be transferred to various types of destinations, such as a computer, smartphone, electronic tablet, or website, for purposes of generating Figures of Merit and an Airway Management Report. In some embodiments, the post-event data review (incorporating the Airway Management Report and associated Figures of Merit of the present invention) may occur directly on the monitor-defibrillator itself, at the conclusion of the procedure or at the end of the patient care encounter, without any need to download or transmit the data to a remote location. In yet other embodiments, the post-event data review may occur on any communicatively coupled electronic device display, at any point in time after the conclusion of the procedure, with data from the monitor-defibrillator transmitted to a remote location (such as a cloud data storage and processing location) and with derived Figures of Merit and additional Airway Management Report content then transmitted to the communicatively coupled electronic device display.

FIGS. 2(a), 2(b), 2(c) and 2(d) are flow charts or flow diagrams illustrating one or more processes, methods, functions or operations that may be performed in implementing an embodiment of the systems and methods described herein. As will be described in greater detail, these Figures are flow charts or flow diagrams illustrating a few example permutations of the data processing flow that may be used to derive a specific Figure of Merit. As noted, in general, the Figures of Merit (FOM) referred to or described herein may be considered: (1) the % of a time interval of specific and critical clinical significance where specific criteria (of either signals from one or more sensors, or parameters derived from those signals) are met, (2) a representation of the distribution of signal characteristics or parameter values within that time interval of specific and critical clinical significance, or (3) the minimum or maximum value of a physiologic parameter measured during the time interval of specific and critical clinical significance.

Figure 2A:
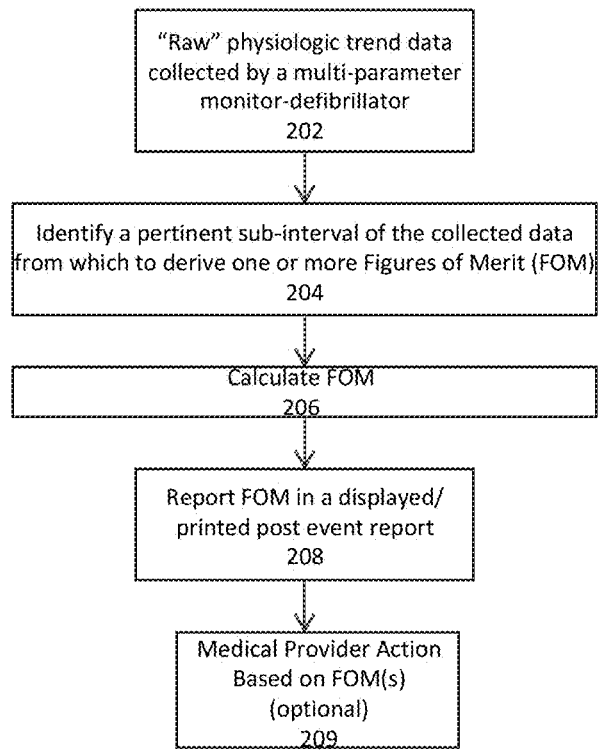
FIGS. 2(a), 2(b), 2(c) and 2(d) are flow charts or flow diagrams illustrating one or more processes, methods, functions or operations that may be performed in implementing an embodiment of the systems and methods described herein.

With reference to FIG. 2(a), at step or stage 202, "raw" physiologic trend data (referring to an unprocessed sequence of vital signs trend values as recorded and stored in memory by the monitor—no data cleaning, de-noising, data reliability assessment, etc. has been performed on it as of yet) is collected from one or more sensors by a multi-parameter monitor-defibrillator. Note that the monitor-defibrillator may be of the type described with reference to FIG. 1 or FIG. 3, or may be another form of multi-parameter physiologic monitor, monitor, etc.

Examples of physiologic trend data may include: heart rate (HR), pulse rate (PR), arterial blood oxygen saturation (SpO2), breath rate (RR) (also known as respiratory rate or ventilation rate, depending on the source of the breaths), end-tidal carbon dioxide level (EtCO2), systolic blood pressure (SBP), diastolic blood pressure (DBP), mean arterial pressure (MAP). Additional examples of trend data may include: regional tissue oxygen saturation (rSO2), ventilation tidal volume, ventilation airway pressure, or end-tidal oxygen level (EtO2).

In one embodiment, this physiologic trend data is collected during the course of a patient care event in which a Rapid Sequence Intubation (RSI) procedure was performed. In this context, RSI refers both to traditional RSI as well as variations on the procedure that have been given various names (e.g., Delayed Sequence Intubation, Rapid Sequence Airway, etc.) that all share the common characteristics of (1) one or more medications are administered to a patient to induce anesthesia, (2) an invasive airway device (e.g. tracheal tube, supraglottic airway) is placed in the patient's airway, and (3) positive pressure ventilation is subsequently provided to the patient.

As suggested by step or stage 204, next, a pertinent sub-interval of the collected data from which to derive one or more Figures of Merit (FOM) is identified. This sub-interval identification may be performed by any suitable method or process; options for determining/selecting the pertinent sub-interval include, but are not limited to, a software process automatically determining a relevant sub-interval based upon the data contained in the monitor-defibrillator memory or data file, or a user of the report software identifying one or more key time points from the process-of-care based upon information in the monitor-defibrillator data file, or in other available event documentation. These time points used to define the sub-interval generally consist of discrete events that occur a single time during the process of managing a patient's airway within an overall patient encounter, and effectively represent "boundaries" that distinguish key stages of the emergency airway management process, and that separate these stages from other portions of the overall patient care event, including portions not directly associated with the emergency advanced airway management procedure. Note thus that these time points are not arbitrarily specified by a user, but rather are tied to specific key events within an emergency airway management process.

Examples of data elements that may be available in the monitor-defibrillator memory or data file, and that may help either an automated software process or a user to manually identify such time points, include, but are not limited to: time-stamped event markers (e.g. an "induction medication administered" event) entered into the monitor-defibrillator (and/or entered into a communicatively-coupled device such as an electronic documentation or patient care reporting tablet, a smartphone app, or a different monitor) by a medical provider during the emergency advanced airway management procedure; audio or video data recorded by the monitor-defibrillator or a communicatively-coupled device; time-stamped events associated with changes made by the medical provider to the configuration or mode of the monitor-defibrillator (such as switching the monitor-defibrillator from a mode intended to optimally assist with the process of intubation, to a mode intended to optimally assist with the process of post-intubation ventilation); time-stamped events obtained from, and associated with the use of, another medical device during the patient care event, such as a video laryngoscope, a point-of-care ultrasound system, and IV infusion pump, or a ventilator.

Note also that with respect to providing insight into the quality of the airway management process, information (e.g., certain vital signs values, or derived metrics) may be of no particular significance on one side of the "boundary", and of high (or relatively higher) significance on the other side of the "boundary". Note also that the reliability accuracy, or interpretation of the measured parameters may vary across the boundary due to one or more of several possible reasons; these reasons may include sensor or measurement device operating conditions, patient condition, relevance of parameter to patient condition, etc.

In one embodiment, the important/useful process-of-care-related key time points (that typically only occur once each during the process of managing a patient's airway within an overall patient encounter) include at least: (1) induction of anesthesia, and (2) successful placement of the airway device (e.g., an endotracheal tube). A 3rd time point that may be useful specifically for an EMS-performed RSI would be the time of arrival at the emergency department (conclusion of patient transport). Additional time points of potential utility (depending on the medical care setting) may include: time of initiation of patient transport (for an EMS-performed RSI), time of initiation of pre-oxygenation, time of initiation of laryngoscopy, and time of hand-off of the patient to the next care location and/or team.

Next, at step or stage 206, a Figure of Merit may be determined, calculated, generated, etc. As mentioned, the Figures of Merit (FOM) referred to or described herein may be considered: (1) the % of a time interval of specific and critical clinical significance where specific criteria (of either signals from one or more sensors, or parameters derived from those signals) are met, (2) a representation of the distribution of signal characteristics or parameter values within that time interval of specific and critical clinical significance or (3) the minimum or maximum value of a physiologic parameter measured during the time interval of specific and critical clinical significance. In one or more embodiments, the generated summary report depicts trend data for the entire interval that data are available, and for any and all of the monitored parameters. Thus, in some embodiments, the report includes one or more figures-of-merit (FOM), derived from one (or more) of the monitoring parameters, and measured over a specific subset of the overall interval that the constituent parameter(s) contributing to the figure-of-merit were monitored. The purpose/value of the Figures of Merit is that they reflect either: (1) patient stability and/or safety during the specified time interval (which, as noted, may be an interval of specific significance and meaningfulness, because it was derived based on the specific key care process events that define (serve as boundaries for) the important phases of the care process), or (2) an aspect of the quality (e.g. adherence to the clinical protocol, or to generally accepted best practices) with which the procedure was performed.

After calculation or determination of the Figure of Merit, the FOM is displayed, printed, and/or otherwise provided to a medical provider (as suggested by step or stage 208). This presentation may be in the form of a post event report that aggregates multiple FOMs, with optionally additional information such as described in FIG. 4. The medical provider then may take action based upon the information provided by the FOM, the aggregation of FOMs, and/or the overall post-event report, as suggested by step or stage 209.

Examples of medical providers that may be provided with the FOM, and example actions they may consequently take include:

(1) The FOM may be provided to the medical provider (for example, a paramedic or a doctor) who performed or directed the emergency advanced airway management procedure. The FOM indicates an aspect of the quality or safety of the emergency advanced airway management procedure, and the medical provider will thus be provided with insight into the quality and/or safety of their patient care that they would not have known without the FOM. If the FOM indicates suboptimal quality or safety, then the medical provider can then reflect upon the patient care event, and their performance during the event, to identify contributors to the suboptimal quality or safety revealed by the FOM. The provider may then seek additional education or training to better prepare for those aspects of their next emergency advanced airway management procedure, or may adjust their mental approach, their patient care strategy or their clinical decision-making during the next procedure (such as by utilizing different procedural tools or techniques, or by communicating and interacting differently with other providers who are part of the immediate patient care team). Such performance improvement measures, which beneficially impact the care of all future patients cared for by the provider, are contingent upon the FOM, which by identifying a specific aspect of suboptimal quality or safety, allows appropriate targeting of specific performance improvement measures.

(2) The FOM may be provided to a medical supervisor (for example, a training officer, or a preceptor of the provider) who performed or directed the emergency advanced airway management procedure. Since the FOM indicates an aspect of the quality or safety of the emergency advanced airway management procedure, the FOM may be used by the medical supervisor during a debriefing of the procedure to highlight an aspect of the patient care process that was exemplary and thus deserving of recognition, and/or to highlight an aspect of the patient care process that was deficient or hazardous, and thus meriting an analysis of contributory factors or a quality improvement intervention targeting that specific deficiency or hazard. For example, if a Figure of Merit describing the proportion of time during the emergency airway management procedure that pulse oximetry was monitored reveals that pulse oximetry was not in fact monitored during a significant proportion of the procedure (a fact that the provider may have been oblivious to during the procedure, due to human factors challenges such as task fixation and loss of situational awareness), then the medical supervisor may then identify that this lack of monitoring was a consequence of, for example, failure to confirm the status of monitoring before initiating the procedure. Performance improvement can then be achieved in future procedures by such quality improvement interventions as implementation of a pre-procedural checklist, assigning a different provider to attend to and ensure monitoring adequacy throughout the procedure, or use of a different pulse oximetry sensor that is less likely to become dislodged, etc.

As another example, if a Figure of Merit describing the proportion of time that SpO2 values were below 90% during the critical sub-interval between induction of anesthesia and successful placement of an advanced airway reveals that SpO2 values were below 90% for a significant proportion of that critical sub-interval, then the medical supervisor may then identify that this episode of oxygen desaturation (which may have been unrecognized by the medical provider performing the procedure; published literature indicates that both oxygen desaturation, and provider unawareness of oxygen desaturation, are very common) was a consequence of, for example, inadequate pre-oxygenation duration, inappropriate pre-oxygenation technique, or an inappropriately prolonged intubation attempt. Performance improvement can then be achieved in future procedures by such quality improvement interventions as adjustments to pre-oxygenation strategy, establishing a minimum pre-procedural SpO2 threshold indicative of adequate pre-oxygenation as a requirement to proceed with the procedure, or assigning a different provider to continuously watch the SpO2 values and alert the provider performing the procedure immediately and continuously upon SpO2 falling below 90%.

(3) The FOM may be provided to a medical director, such as a medical program director of an EMS agency. In many EMS agencies, such as those in the United States, emergency advanced airway management procedures are performed by paramedics, who provide medical care under the license of the agency medical director. Since the medical director is not present in the pre-hospital setting during an emergency advanced airway management procedure, the medical director's knowledge of the details of how a procedure was performed in a given patient, including important aspects of the quality and safety of the procedure, is severely limited by the nature of the typical documentation, as described previously. In this context, the FOM provides unique insight into otherwise hidden aspects of the quality or safety of the emergency advanced airway management procedure. Based upon this insight, the medical director may take a number of important actions, such as: revision of clinical protocols to address a pattern of deficiency revealed by the FOM, identification of individual providers who may require additional training or education to achieve performance improvement on the aspect of the procedure targeted by the FOM, or implementation of new or different medical equipment designed to improve the quality or safety of the aspect of the procedure targeted by the FOM.

(4) The FOM may also be entered into a medical registry, along with other patient and event information. In this example, the FOM is aggregated across many patients, and also potentially across different healthcare operations (such as EMS systems, or hospitals), allowing benchmarking of individual providers, or individual operations, against peers and against the aggregate data set.

An important aspect of the Figure(s) of Merit, and what enables them (and thus the overall Airway Management Report) to provide value to a user, is that they are only calculated once a critical sub-interval of significance to the emergency airway management procedure has been defined. This is because outside of this interval (e.g., prior to the induction of anesthesia or a boundary of another critical sub-interval), the Figure(s) of Merit may have an ambiguous meaning or may have no particular relevance to the safety and quality of the emergency airway management care process; it is only within the critical sub-interval that the Figure(s) of Merit have a clear, unambiguous, and clinically valuable meaning related to patient safety and/or to the quality of care in the emergency airway management process.

For example, the oxygen saturation values (or blood pressure values, etc.) prior to the time of induction of anesthesia represent an unknown combination of the patient's presenting state of illness, and initial attempts to treat and stabilize the patient. It is only after the time point at which the medical provider has decided they are going to perform an RSI procedure, and has progressed to the step of induction of anesthesia, that the oxygen saturation values (or blood pressure values, etc.) are unambiguously the responsibility of the medical provider. It is only during the critical sub-interval of the physiologic monitoring data collected from the overall patient encounter, bounded by this time point of induction of anesthesia, that any abnormalities or derangements in the physiologic monitoring values provide clear and direct insight into the quality of the emergency airway management process, and patient safety during that process.

Figure 2B:
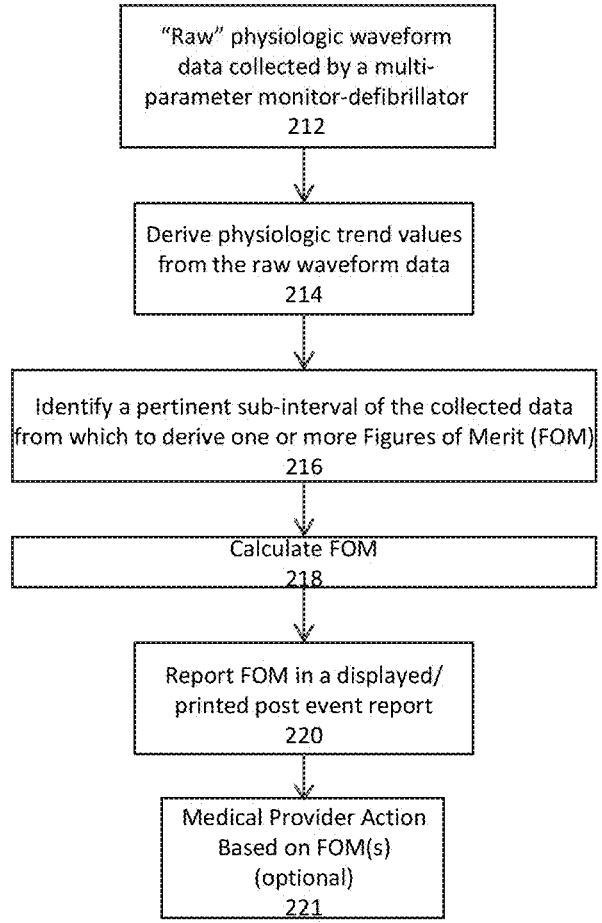

With reference to FIG. 2(b), at step or stage 212, "raw" physiologic waveforms recorded by the monitor are collected (rather than the raw recorded physiologic trend values referred to in FIG. 2(a)), and the additional step 214 represents a process or operation to derive the physiologic trend values from the recorded waveforms. Note that, depending on the monitor, and the quality/accuracy of its raw physiologic trend data values, it will sometimes be possible to achieve improved accuracy and trustworthiness of the physiologic trend values by deriving them as a subsequent step (e.g., the software process or algorithm(s) used to derive, compute, or determine the FOM could utilize a different algorithm than the one native in the monitor to derive the trend values from the waveform data). Following this derivation of the trend values, a pertinent sub-interval is identified at step or stage 216, in a manner similar to that described with reference to step or stage 204 of FIG. 2(a). At step or stage 218, one or more FOMs are derived, calculated, or determined. After calculation or determination of the Figure of Merit, the FOM may be included in a post-event report which is displayed, printed, and/or otherwise provided to a medical technician or professional (as suggested by step or stage 220). As described with reference to FIG. 2(a), after generation of the post-event report (or a specific FOM), the medical provider then may take action based upon the information provided by the FOM, the aggregation of FOMs, and/or the overall post-event report, as suggested by step or stage 221.

Figure 2C:
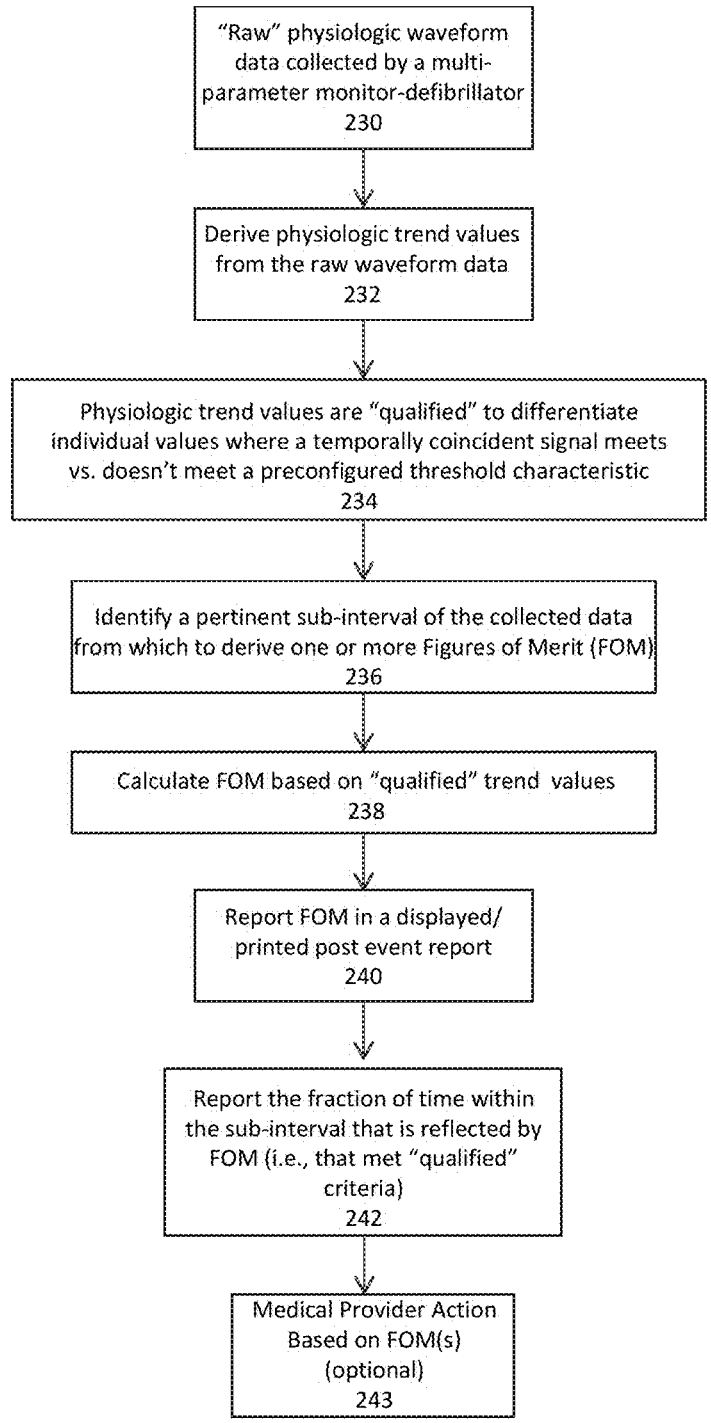

With reference to FIG. 2(c), this process flow illustrates the addition of an aspect of "qualifying" the trend data values prior to plotting the trend graph. A benefit of "qualifying" the raw trend values is because the raw trend data values may not always be reliable or accurate. For example, there may have been noise or artifact(s) in the source waveform from which the physiologic trend values were derived. Multi-parameter physiologic monitors, such as the monitor-defibrillators discussed herein, typically will display and log physiologic trend data values even when there is a significant amount of noise or artifact present in the source waveform. For example, there may be a significant amount of noise or motion artifact in the ECG waveform, but the monitor will still display a heart rate derived from that noisy/artifacted waveform. In such a case, the heart rate will often be intermittently incorrect. It is generally understood by medical providers that the best practice is to look at the ECG waveform to make sure that the signal quality is adequate before accepting that the heart rate value derived from the ECG waveform is accurate or reliable. This is relatively easy to do in real time when viewing a monitor. However, when viewing just derived trend data after the event, there is no ready means of doing this data quality verification. Addressing this limitation is the purpose of certain of the steps in the flowchart of FIG. 2(c).

As stated above, the source waveforms associated with some of the common physiological parameters monitored by a monitor-defibrillator may be compromised during portions of a patient monitoring episode (including during the critical sub-interval associated with the emergency airway management process), leading to potentially unreliable or inaccurate trend values. This can especially occur in the prehospital environment, where environmental variations, movements of the patient and EMS providers, motion related to the ambulance transport of the patient, and specific treatments or aspects of the care being provided to the patient can all affect the characteristics and/or signal quality of the physiologic waveforms. This can result in periods of time during which the physiologic trend values derived from the physiologic waveforms become inaccurate or less reliable. Examples of ways in which the waveforms may be compromised, include, but are not limited to:

The ECG waveform is typically the source for heart rate values, and noise (e.g., electrical interference) or an artifact (e.g., an artifact from patient motion or tenuously attached electrodes) in the ECG signal can result in incorrect heart rate values;

The photo-plethysmograph waveform produced by a pulse oximeter is a source for pulse rate values, and also is a component of the information used to derive oxygen saturation (SpO2) values. Poor signal quality in the photo-plethysmograph (e.g., from a poorly placed or attached sensor, patient motion, or poor perfusion to the part of the patient's body where the sensor is placed) can result in the pulse oximeter reporting pulse rate and oxygen saturation values that are unreliable;

The capnography waveform (reflecting the concentration of carbon dioxide measured in the patient's airway continuously throughout the breathing cycle) is the source for end-tidal carbon dioxide (EtCO2) and breathing rate (RR) values. The capnography waveform can be impacted in ways that may make the EtCO2 and/or RR values inaccurate reflections of the true physiologic status they are intended to represent. As one example, when there is a sufficiently large leak in the airway, the EtCO2 values measured by the capnography sensor are decreased, even though the actual lung alveolar CO2 concentrations may not have changed. This increase in the alveolar CO2 to end-tidal CO2 gradient can be misleading to a user, who may incorrectly interpret the decrease in EtCO2 as being caused by a change in the physiologic status of the patient, rather than a change in the status of the equipment and apparatus connecting the patient's airway to the monitor.

Similarly, other causes of dilution of the sampled gas, breathing asynchrony (where both the patient and an external source of positive pressure ventilation are creating breaths) or chest compressions performed during CPR can all create artifacts or abnormalities in the capnography waveform resulting in less accurate or less reliable EtCO2 and/or RR measurements.

With reference to FIG. 2(c), at step or stage 230, "raw" physiologic waveforms recorded by the monitor-defibrillator are collected (as at step or stage 212 of FIG. 2(b), and again as opposed to the raw recorded physiologic trend values referred to in FIG. 2(a)). Step or stage 232 represents a process or operation to derive the physiologic trend values from the recorded waveforms. At step or stage 234, the physiologic trend values are "qualified", in order to indicate or exclude those values that may be unreliable or incorrect. This may be accomplished by applying an algorithm (and one that is typically different from any algorithm that might be associated with the monitor-defibrillator or MPMD) to the source waveform associated with a physiologic trend value. This algorithm is intended to recognize the feature(s) of the waveform responsible for the unreliability/inaccuracy of the derived physiologic trend values. For example, a noise-detection algorithm may be applied to the ECG waveform. The algorithm output would identify one or more periods of time during which there was a significant noise/artifact on the ECG waveform. As an example, the heart rate values during these periods of time would then be omitted from the heart rate trend graph on the Airway Management Report.

In an alternate embodiment, the heart rate values during the periods of "low reliability/potential inaccuracy" would still be plotted in the trend graph, but an indication would be provided that those periods are less reliable and potentially inaccurate. Such indication could be by use of almost any common means of distinguishing portions of a line graph—e.g., colors, line style or thickness, shading, labels, etc.

A value of one or more embodiments that include this data qualification step stems from the fact that in the clinical circumstances in which emergency RSI and subsequent ventilation support is performed, environmental and scene conditions are highly variable, and there is frequently a lot of activity with and around the patient. Because of these factors, noisy/artifacted signals in the physiologic monitor are common, resulting in trend data values that are often unreliable or inaccurate for portions of time.

Next, as described with reference to FIGS. 2(a) and 2(b), a pertinent or relevant sub-interval is identified at step or stage 236, in a manner similar to that described with reference to step or stage 204 of FIG. 2(a).

At step or stage 238, the FOMs are calculated using the qualified physiologic trend values from step or stage 234 (and not the raw values as in the embodiments described with reference to FIGS. 2(a) and 2(b)). After calculation or determination of the Figure(s) of Merit, the FOM may be included in a post-event report which is displayed, printed, and/or otherwise provided to a medical technician or professional (as suggested by step or stage 240).

Note that as suggested by step or stage 242, the portion of time within the interval defined in step 236 which was used to calculate the FOM is reported. For example, if there was noise affecting the ECG signal 10% of the time interval between the "induction of anesthesia" time point and the "arrival at the ED" time point, then heart rate data would be omitted/ignored from that 10% of time, meaning that any FOM incorporating heart rate data (e.g. lowest heart rate during the interval) would have been calculated using heart rate data from 90% of the interval. That 90% value would be reported in association with any ECG-derived FOMs on the Report. In an alternate embodiment, the portion of time excluded (rather than included) in the FOM calculation would be reported (i.e. 10%, in this example). As described with reference to FIG. 2(a), after generation of the post-event report (or a specific FOM), the medical provider then may take action based upon the information provided by the FOM, the aggregation of FOMs, and/or the overall post-event report, as suggested by step or stage 243.

Figure 2D:
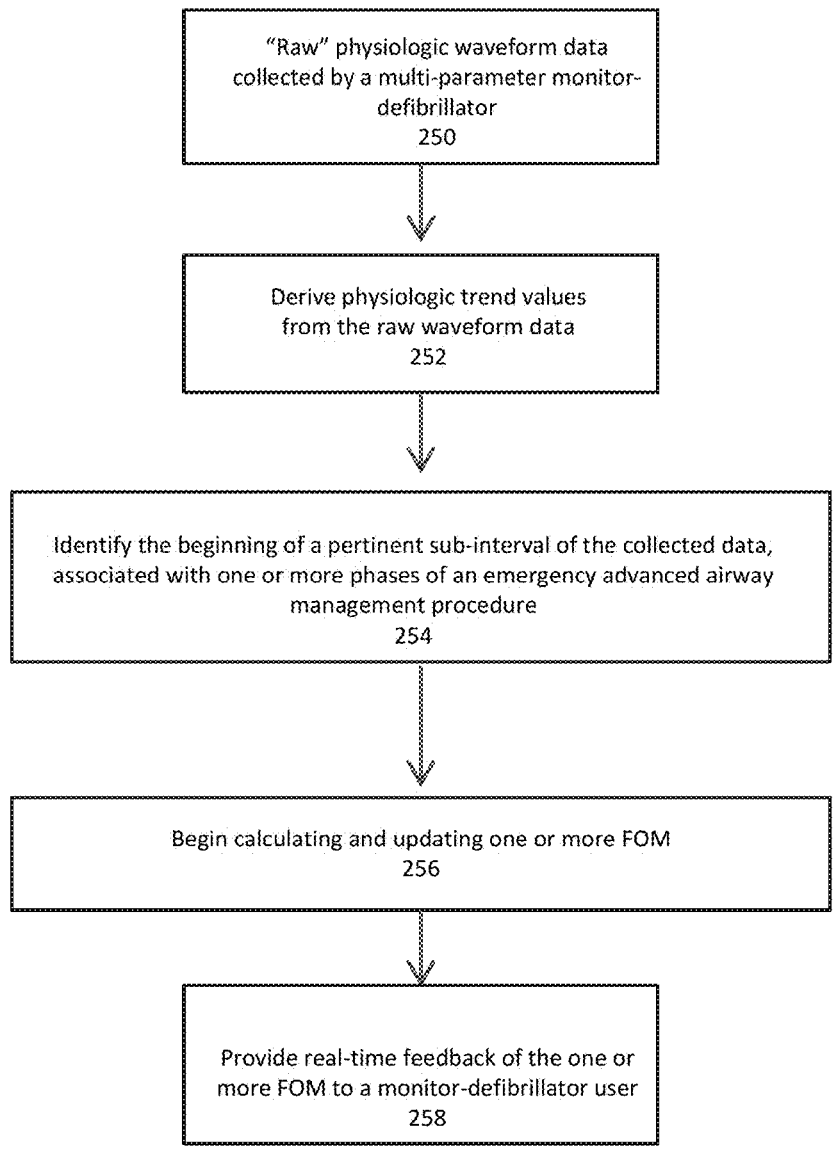

With reference to FIG. 2(d), this flowchart is directed to a process involving the real-time monitoring of one or more FOM that are generated during the provision of a medical service or procedure. As shown in the figure, at step or stage 250, "raw" physiologic waveforms recorded by the monitor-defibrillator are collected. At step or stage 252, physiologic trend values are derived from the raw waveform data. Next, at step or stage 254 the process identifies the beginning of a pertinent sub-interval of the collected data, where the sub-interval is associated with one or more phases of an emergency advanced airway management (or in some cases, other) procedure. The process then calculates, derives or determines one or more relevant FOM(s) and updates those values, as suggested by step or stage 256. Note that the updating may be performed as a continuous process or as one that is triggered by an event or passage of time. The FOM(s) are provided as feedback during the procedure to a user of the monitor-defibrillator, as suggested by step or stage 258.

Figure 4A:
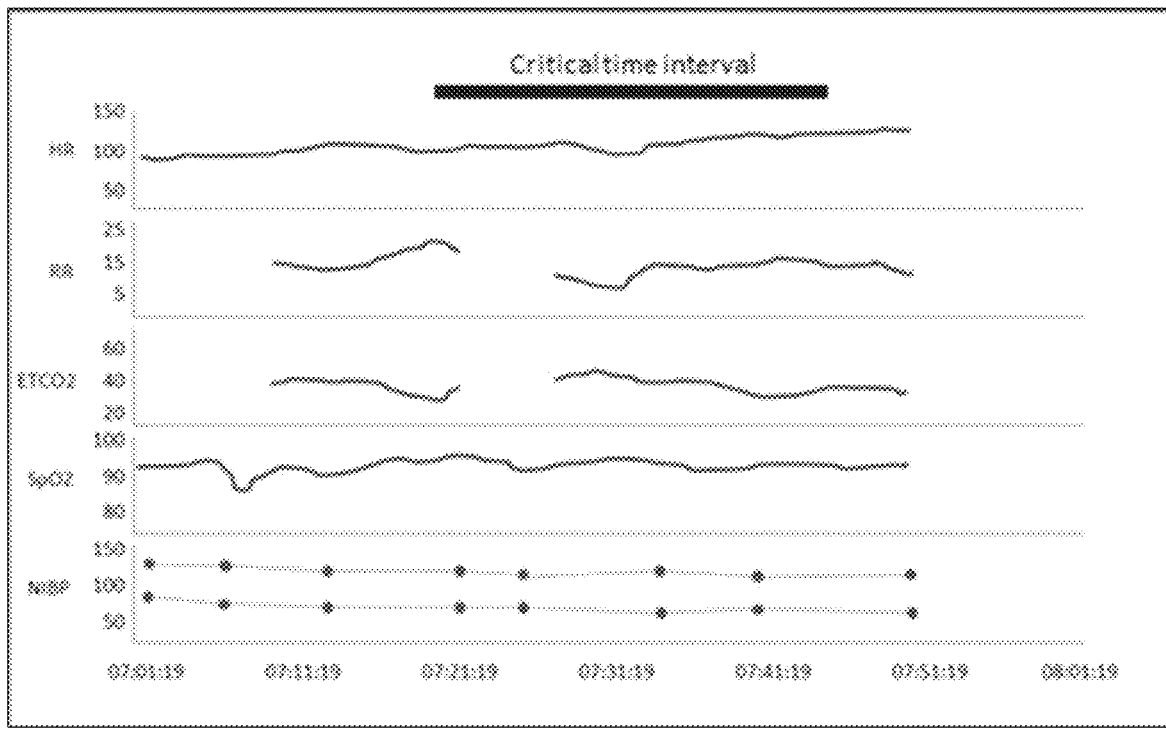

FIGS. 4(a), and 4(b) are examples of aspects or portions of a summary report or display that may be generated in whole or in part by an embodiment of the systems and methods described herein. Note that in these examples, the numbers and values in the different portions and elements of the report do not necessarily agree with each other—the numbers and values are included as general illustrations of the type of information included in the report, and are not intended to reflect the accurate mathematical relationships that would exist between depictions of measurements and intervals across different portions or elements of the report. Note also that in these examples, the FOMs and other information are generally presented as text numbers and values, but in other embodiments, these numbers and values could be presented via other common means of graphically summarizing information, such as graphs, charts, icons, etc. Note additionally that in these examples, certain values are illustrated representing thresholds determining how physiologic measurements are categorized for purposes of calculating the associated FOMs (e.g., which measurement values are categorized as being within normal limits, versus above or below normal limits). In some embodiments, these threshold values are intended to be configurable by a user—e.g., in element 408, the oxygen saturation threshold of 90%, which serves as the threshold between "within normal limits" oxygen saturation values and below normal limits oxygen saturation values, would be configurable by a user, such that they could instead change the threshold to, for example, 93%.

As shown in FIG. 4(a), in one example of the summary report 400, a header section (identified as element 402 in the figure) may be part of the report. The header section will typically include information regarding the event, the device or apparatus used to collect data, the device configuration, the date and time of the event, etc. Element 404 of FIG. 4(a) is an example of a presentation of trend data for specific vital signs (such as HR, RR, and those listed along the left vertical border of the graph) that may be part of a summary report, or may be generated in addition to a summary report. The presentation of trend data includes an indication (a shaded and labeled horizontal bar, in this example) of the critical sub-interval from which the FOMs (incorporated into the other elements of the summary report) are derived. A "Monitoring Use" section (406) provides FOM information, generally regarding the proportion of the critical sub-interval over which the patient's various physiologic parameters were monitored, expressed as a percentage of the "critical time interval".

FIG. 4(b) is an example of additional aspects or portions of the summary report, incorporating FOMs specific to the critical sub-interval of the patient encounter reflective of the emergency airway management procedure. These include sections providing FOMs related to the oxygenation status (element 408) and the ventilation status (element 410) of the patient during the critical sub-interval. These FOMs indicate the % of time during the critical sub-interval that oxygenation/ventilation measurements were within normal limits, below normal limits, above normal limits, or missing. An additional section (element 412) provides FOMs indicating the number of episodes and duration of specific vital signs derangements during the critical sub-interval. An additional section of the report (element 414) provides information related to the distribution of breath rates measured during the critical sub-interval.

Note that the exact time point associated with any of the events that serve as boundaries to define a pertinent sub-interval may not be precisely known. For example, for purposes of generating an Airway Management Report from a specific patient encounter, the information used by the person generating the Report to identify the time at which the "induction of anesthesia" step was performed may be a written (or electronically documented) record of the procedure, and the time stamps used to document events in that record may be quantized to whole minute increments. So for example, the record of the procedure may indicate that "induction of anesthesia" was performed at 11:25 AM, but it was really performed at 11:25 and 34 seconds, with respect to the physiologic waveforms and trend data recorded by the monitor during the patient care event. Thus, there is inevitably a little bit of imprecision in the identification of the event time points used to bound the pertinent sub-interval for purposes of calculating the FOM(s). It should be appreciated that there are other potential sources of time stamp imprecision, depending on the method used to identify the time points for purposes of generating an Airway Management Report. For example, the clock used by the provider performing the procedure to note the time of "induction of anesthesia" may have been a wristwatch that was one minute behind the time on the physiologic monitor. Also, many of these events are not instantaneous actions, but rather an action that takes a certain period of time—e.g. "induction of anesthesia" involves drawing up several medications into syringes, and then administering those to the patient in sequence over a certain short (e.g., one minute) but not instantaneous period of time. In this example, the event time might variously be considered and/or recorded as the beginning of administering the first drug, the conclusion of administering the last drug, etc. This introduces uncertainty into the event times that are noted and hence into the identification of the critical interval(s).

Given the above, it is important to note that a time or time stamp being used to identify a stage of a particular event associated with treating a patient may not be completely accurate in terms of it being precisely the time when the stage or event occurred. Thus, some uncertainty in the accuracy of the times recorded and how they are used may be introduced. Thus, it should be understood that the times and time intervals being used in embodiments of the system and methods described herein may not correspond exactly to those of an actual event or stage of an event or treatment.

As described, in some embodiments, the software modules or processes executed by an electronic processor or processing element as part of the system and methods described herein generates an Airway Management Report, where such report may include, but is not limited to (or required to include), one or more of the following components:

1. Graphical trend data for one or more of the monitored physiologic parameters, such as Heart Rate, Oxygen Saturation, Respiration/Ventilation Rate, End-tidal CO2, and Blood Pressure, depicting for each parameter the entire interval that was monitored (i.e., for which data was obtained, which as described herein, may be selected or determined for only a subset of the overall treatment time interval);
2. Indications on the trend data graphical representation of one or more key events associated with the airway management process, for example an event or events such as:
   a. Time of initiation of pre-oxygenation;
   b. Time of induction of anesthesia;
   c. Time of initiation of laryngoscopy and attempted placement of an advanced airway;
   d. Time of successful placement of an advanced airway;
   e. Time of initiation of patient transport; or
   f. Time of hand-off of the patient to the next care location and/or team.
3. At least one figure-of-merit (FOM) derived from an interval between two of the key events, as exemplified above. For example, a figure-of-merit that indicates the proportion of the interval between time of induction of anesthesia and time of hand-off of the patient to the next care location and/or team (e.g. arrival at the emergency department, for an EMS-performed RSI) that pulse oximetry monitoring was actually occurring (even though pulse oximetry monitoring may have started before induction of anesthesia, and may also have continued after arrival at the ED).

In some embodiments, elements of an embodiment of the Airway Management Report may include:

- a depiction or illustration of multi-parameter trend data from a patient care event;
- an indication on (or alongside) the trend data of the time point(s) of one or more key events associated with the airway management process that occurred during the patient care event; or
- one or more figures-of-merit (FOM) representative of an aspect of one or more of the airway management care process, care quality, or the patient's physiologic response to the airway management care, where the figure(s)-of-merit are derived from a specific sub-interval of the available trend data, with the specific sub-interval demarked by one or more of the indicated key events.

Note that the physiologic trend data may plot trend values as recorded by the monitor-defibrillator, or in some embodiments, the trend data depicted on the report may be (re) derived in the post-event software (or some other computing environment external to the monitor-defibrillator itself) by applying one or more algorithms to either the original trend data recorded by the monitor-defibrillator, or to the raw physiologic waveform data that is the basis for the trend data. Note that a value of re-deriving the trend data in the post-event software is one or more of: improving the accuracy and/or resolution of the trend data; removing noise and artifact(s) from the trend data; or deriving a variation of the monitoring parameter that is more clinically meaningful and actionable than the manner in which the parameter is derived and reported on the monitor-defibrillator itself.

For example, while the monitor-defibrillator may record Heart Rate trend data derived from a monitored ECG lead using an algorithm in the monitor-defibrillator, the Heart Rate data depicted in the trend data component of the post-event report might be derived by a different algorithm in the post-event report software, which may operate to process one or more of the available ECG signals and derive Heart Rate trend data that may differ from the Heart Rate trend data recorded during the event by the monitor-defibrillator. For example, the two types of data might differ because a different, more optimal, ECG lead was used for deriving Heart Rate in the post-event report, or because the ECG lead used for derivation of Heart Rate was dynamically adjusted by the software to always select the most optimal of the available ECG leads, or because a noise filtering/removal algorithm was applied to the ECG by the post-event software, or because an artifact detection algorithm was applied to the ECG by the post-event software, allowing it to suppress/avoid reporting of likely erroneous values during periods of critical artifact.

As another example, while the monitor-defibrillator may record "breath rate" (usually labelled RR for "Respiratory Rate" on monitors), trend data derived from the capnography CO2 waveform, the post-event report could depict a "breath rate" trend with different values than those displayed/recorded on the monitor, where the breath rate trend is derived by an algorithm in the post-event report software that processes the capnography CO2 waveform in a manner different from how the CO2 waveform is processed in the monitor-defibrillator. In this case, the algorithm in the post-event report software might be designed to allow better discrimination between true positive-pressure ventilations provided by the EMS personnel vs. spontaneous breathing efforts initiated by the patient. As a result, the post-event software could report breath rate values closer to the true rate of positive-pressure ventilations that were delivered by the medical provider, ignoring the interspersed spontaneous patient breaths that may also be incorporated into the RR which is reported on the monitor. Thus, the breath rate reported on the post-event report may be lower than the breath rate that was displayed in real time on the monitor, and the post-event breath rate would more specifically reflect the actual ventilation rate performed by the care provider, which is an important aspect of patient safety and care quality associated with the emergency advanced airway management procedure.

Figures-of-Merit (FOM) Derived from a Specific Subset of the Overall Monitoring Time As recognized by the inventor, a variety of figures-of-merit (FOM(s)), representative of specific critical subsets of the overall time the patient was monitored, would assist in achieving the goal of facilitating improved audit of the airway management care process and the patient's physiologic response to that care. In one embodiment, these figures-of-merit are calculated in the post-event report software, and depicted on the post-event summary report, along with the physiologic trend data from the overall patient encounter. However, it should be appreciated that these figures-of-merit could instead comprise the entirety of the post-event summary report (i.e. without the accompanying trend data from the overall patient encounter), and/or that these figures-of-merit could be calculated and depicted on another computing device, including the monitor-defibrillator itself, or a communicatively-coupled documentation/event recording device such as an ePCR tablet, a smartphone app, etc.

In any of these embodiments, it should be appreciated that a key element of these figures-of-merit is that they are applied to/derived from a specific critical subset of the overall time interval that the patient was attached (via one or more sensors) to the multi-parameter monitor-defibrillator during the patient encounter. A value and importance of this source of a figure-of-merit is that the figure of merit has an unambiguous clinical significance during this defined sub-interval of time, while that same figure of merit may be deceptive and/or have an uncertain meaning with respect to an assessment of the emergency advanced airway management process when applied to a time interval that includes periods of time outside of this specific sub-interval. Note that the specific critical sub-interval is identified and demarked by one or more of the methods described earlier.

Specific examples of figures-of-merit that may be used to achieve the goal of summarizing the process and quality of an emergency advanced airway management procedure, and/or a patient's physiologic response to the airway management process, are listed below. Note that the list is not intended to be exhaustive or to indicate a required figure-of-merit. For each figure-of-merit, the following is described or intended to be a possible presentation of the information or use case:

1. The derivation of the figure-of-merit based on physiologic (and optionally also event) data recorded by the monitor, time-stamped event data acquired from another electronic source such as an electronic patient care report, or time-stamped event data supplied by a user;
2. Reporting the figure-of-merit in a post-event summary report or data review software;
3. Reporting the figure-of-merit in conjunction with a graphical depiction of the physiologic trend data on which the figure-of-merit is based;
4. Reporting the figure-of-merit on a physiologic monitor (such as a monitor-defibrillator) immediately at, or shortly after (e.g., within 10 minutes) the end of a patient care monitoring event during which an emergency advanced airway management procedure was performed;
5. Reporting the figure-of-merit on a physiologic monitor (such as a monitor-defibrillator) as feedback to a medical provider during a patient care event, including during the portion of the patient care event associated with an emergency advanced airway management procedure; and
6. Transmitting the figure-of-merit, optionally with additional information from the summary report, to a destination remote from the device used to calculate/derive the figure-of-merit.

Potential Figures-of-Merit (FOM)

1) A figure-of-merit describing the proportion of time that a given monitoring parameter was actually being monitored, during a sub-interval associated specifically with one or more stages of the emergency advanced airway management procedure.
a) Examples:
   i) The proportion of the interval between the time of induction of anesthesia and the time of hand-off of the patient to the next care location or team that pulse-oximetry was being monitored;
   ii) The proportion of the interval between the time of successful placement of an advanced airway and the time of hand-off of the patient to the next care location or team that waveform capnography was being monitored;
   iii) The proportion of the interval between the time of induction of anesthesia and the time of successful placement of an advanced airway that cerebral oximetry was being monitored;
   iv) The proportion of the interval between the time of initiation of pre-oxygenation and the time of hand-off of the patient to the next care location or team that blood pressure measurements were being obtained at least every 5 minutes;
   v) The proportion of the interval between the time of induction of anesthesia and the time of hand-off of the patient to the next care location or team that ECG was being monitored.
2) A figure-of-merit representing a "hypoxemia dose index", calculated over a sub-interval of a patient monitoring episode that is associated specifically with one or more stages of an emergency advanced airway management procedure.
   Hypoxemia occurs during many emergency medical care events, and can result in profound harm to a patient. Due to the time-sensitive and chaotic nature of many emergencies, the true extent of hypoxemia can frequently be under-appreciated—it can last for longer, and achieve greater severity, than emergency care providers often recognize. For example, copious clinical research reveals that hypoxemia during rapid sequence induction of anesthesia and attempted endotracheal intubation is substantially more prevalent than appreciated by the EMS, Emergency Medicine, and Critical Care fields that perform emergency intubation. This lack of awareness, and lack of objective measurement of hypoxemia "dose" not only impacts the immediate patient being cared for, but also inhibits scientific progress in understanding the linkages between physiologic derangements such as hypoxemia early in the course of emergency care, and downstream consequences for patient course-of-care and outcomes.

In the current art, characterization of the depth and/or duration of hypoxemia is common. The concept of measuring the "area under the curve" (AUC) of a hypoxemia event has also been described in several publications. AUC provides a simple product of depth and duration, but it weights each increment of both depth and duration equally. Physiologically, the incremental risk of critical deterioration, and perhaps also overt harm, accumulated between 5 and 10 seconds of hypoxemia, vs. between 50 and 55 seconds of hypoxemia, is far from equivalent. Similarly, the incremental risk/harm posed by a desaturation from 90 to 85, vs. between 70 to 65 is likely not similar. Increases in duration and/or depth of hypoxemia thus have a relationship to patient hazard that is nonlinear over sequential increments of duration and/or depth. As a result, there would be value in an index of hypoxemia "dose" that better reflected the non-linearity of patient hazard associated with progression of hypoxemia in the duration and/or depth dimensions.

In this context, a FOM describing a mathematical index that responds in a non-linear fashion to incremental increases in the duration and/or depth of a hypoxemic episode may be of value. Such an index may be characterized or described by one or more of the following:

a) A numerical index derived according to a scheme that weights the severity of the duration and/or depth of a hypoxemia episode using a non-linear weighting that includes one or more inflection points at which the slope of the relationship between the duration and/or depth of hypoxemia and severity weighting changes. For example, time spent with a saturation below 80% could be weighted double the time spent with a saturation between 80% and 90%;

b) The index of (1), but where a severity weighting is applied variably to each one-second and/or 1% increment (or other increment value) within the hypoxemia episode, and then the weighted severity values of each one-second interval are summed to produce an overall severity value for the entire episode;

c) The index could be a dimensionless value (i.e., scaled between 0 and infinity), or could be converted to a fixed scale (e.g. 0 to 100) via a suitable equation or function;

d) The index could apply to each of one or more hypoxemia episodes, or alternately could reflect the total "dose" of all hypoxemia episodes within the critical sub-interval of the overall patient care episode;

e) The index could additionally take into account concomitant changes in other vital signs that are likely reflective of an escalating impact of the hypoxemia episode, or that worsen the physiologic impact of a given hypoxemia episode.
1. For example, a change in heart rate or the emergence of abnormal cardiac rhythm activity (e.g., ectopic beats, bigeminy, heart block) during a hypoxemia episode could be used to modify the severity weighting of the affected time interval, in addition to or instead of any weighting already assigned based on the dynamics of the oxygen saturation profile itself;
2. Similarly, the level of, and/or changes in, systolic or mean arterial blood pressure could contribute to or modify the severity weighting of the affected portion of a hypoxemia episode. This blood pressure input could come from either invasive or non-invasive techniques, could be continuous or intermittent, and could be measured by the same monitor or another communicatively-coupled blood pressure measurement device;
3. These modifications of the index based on additional vital signs/physiologic signal input could be in the form of one or more inflection points at pre-defined levels of progressively worsening conditions. For example, one or more inflection points at progressively lower blood pressures below normotension at which, for example, a pre-specified "hypotension multiplier" is applied to the index value, reflecting the fact that concurrent hypotension substantially worsens the physiologic impact of a given oxygen desaturation event;

f) The index output could also be modified (by e.g., adjusting the weightings or non-linearity of index components) based on acute or chronic medical conditions of the patient (e.g., anemia, cardiac or pulmonary disease), with the data on such conditions obtained from user entry of such patient data directly on the monitor providing the index, or obtained from a communicatively-coupled medical record such as on an ePCR tablet, or retrieved from a remotely-hosted electronic medical record (such as in the cloud, or at a hospital);

g) In one embodiment, the index is based on arterial oxygen saturation data as measured by a pulse oximeter. In an alternate embodiment, the index could be based on region tissue oxygen saturation (rSO2) data, as measured by a regional tissue oximeter, or based on a combination of SpO2 and rSO2 data.

3) A figure-of-merit representing the highest or lowest measured value of a physiologic monitoring parameter during a sub-interval (of the overall patient encounter interval) in which clinical best practices would define the absolute value of (or relative normality of) that parameter to be of heightened significance to the quality of the care process and/or to the physiologic response of the patient to the care process.

a) Examples include, but are not limited to:
i) The highest arterial oxygen saturation measured between the time of the beginning of pre-oxygenation and the time of induction of anesthesia;
ii) The lowest arterial oxygen saturation (or alternately, cerebral oxygen saturation) measured between the time of induction of anesthesia and the time of successful placement of an advanced airway;
(1) Note that for a physiologic measurement such as peripheral arterial oxygen saturation that exhibits a physiologic latency (between the time at which that saturation value actually occurred in the central circulation and the time at which it is measured in the peripheral circulation), the time point of one or both of the sub-interval boundaries might be adjusted by a pre-determined fixed amount to account for such latency. For example, the software might identify the time of successful intubation via an aforementioned method, and then extend the end of the sub-interval representing "the time of induction of anesthesia to the time of successful placement of an advanced airway" by one minute, to account for the latency of the peripheral arterial oxygen saturation measurement in response to the achievement of successful intubation and initiation of ventilation;
iii) The lowest (and/or highest) blood pressure measured between the time of initiation of pre-oxygenation to the time of successful intubation (or alternately, a time point that is a fixed 5 minutes after the time of successful intubation);

iv) The lowest (and/or highest) heart rate measured between the time of induction of anesthesia and the time of successful intubation;
v) The highest end-tidal O2 (end-tidal oxygen concentration) measured between the time of initiation of pre-oxygenation and the time of induction of anesthesia;
vi) The highest airway pressure measured between the time of successful intubation and the time of hand-off of the patient to the next care location and/or team; or
vii) The highest tidal volume measured between the time of successful intubation and the time of hand-off of the patient to the next care location and/or team.

4) A figure-of-merit calculated over a sub-interval of a patient monitoring episode that is associated specifically with one or more stages of an emergency advanced airway management procedure and representing the proportion of time during this sub-interval that a given monitored physiologic parameter (or a Boolean combination of parameters) was measured to be within a pre-specified range of values.

Note that in the following examples, the specific values shown represent pre-specified values that are intended to be adjustable/pre-configurable by the user of the post-event software and/or the monitoring device.

Examples include, but are not limited to:
i) The proportion of time between the time of induction of anesthesia and the time of hand-off of the patient to the next care location and/or team that the arterial oxygen saturation was above (or below) 90%;
ii) The proportion of time between the time of successful placement of an advanced airway and the time of hand-off of the patient to the next care location and/or team that both the breath rate was greater than 12/min AND the EtCO2 was less than 35 mmHg;
iii) The proportion of time between the time of successful placement of an advanced airway and the time of hand-off of the patient to the next care location and/or team that both the breath rate was less than 10/min AND the EtCO2 was greater than 45 mmHg;
iv) The proportion of time between the time of initiation of pre-oxygenation to the time of hand-off of the patient to the next care location and/or team that the cerebral oxygen saturation was above (or below) 60%;
v) The proportion of time between the time of successful intubation and the time of hand-off of the patient to the next care location and/or team that the breath rate was between 10/min and 12/min;
vi) The proportion of time between the time of successful intubation and the time of hand-off of the patient to the next care location and/or team that EtCO2 was between 35 mmHg and 45 mmHg;
vii) The proportion of time between the time of successful intubation and the time of arrival at the ED that airway pressure was greater (or lower) than 35 cmH$_2$O;
viii) The number of blood pressure measurements between the time of successful intubation and the time of arrival at the ED where the SBP was lower than 90 mmHg (or the MAP was lower than 65 mmHg); or
ix) The proportion of time between the time of induction of anesthesia and the time of arrival at the ED that the rSO2 was below (or above) 60%.

5) A figure-of-merit calculated over a sub-interval of a patient monitoring episode that is associated specifically with one or more stages of an emergency advanced airway management procedure representing the proportion of time during the sub-interval that a given monitored physiologic signal exhibited a certain feature of significance to the interpretation of the quality of the care process and/or to the physiologic response of the patient to the care process.

a) Examples:
 i) The proportion of time between the time of successful placement of an advanced airway and the time of hand-off of the patient to the next care location or team that the CO2 waveform exhibited evidence of:
  (1) spontaneous respiratory activity;
  (2) airway leak;
  (3) cardiogenic or chest compression induced oscillations;
  (4) Non-plateauing breath waveforms (capnography waveform substantially or completely lacks a phase III);
 ii) The proportion of time between the time of induction of anesthesia and the time of successful intubation that the ECG signal exhibited evidence of:
  (1) Ventricular ectopy;
  (2) A/V block;
  (3) QRS morphology changes such as QRS widening; or
  (4) Tachyarrhythmia or bradyarrhythmia
b) Related to the above examples, the figure-of-merit could represent the presence of a single described feature, or alternately a Boolean combination of two or more of the described features. For example, the ECG features of ventricular ectopy, A/V block, and QRS widening could be combined into a composite "cardiac instability indicator" or "cardiac instability index" (see below). As another example, the CO2 waveform features of spontaneous respiratory activity, airway leak, non-plateauing waveforms, and chest compression induced oscillations could be combined into a "ventilation abnormality indicator" or "ventilation abnormality index". In this manner, the indicator or index would give a clinical reviewer/auditor rapid context about the morphologic characteristics (and in turn the care process effectors of those morphologic characteristics) of the CO2 waveform without needing to go through the process and take the time to actually manually review the continuous CO2 waveform (though the presence of ventilation abnormality may be a useful prompt for the reviewer to take the extra step to review the CO2 waveform, while the absence of ventilation abnormality may provide reassurance that review of the CO2 waveform is not needed because it is substantially normal).
c) The above physiologic signal "features of significance" can also/alternately be calculated in a continuous fashion as "derived parameters" (rather than as a single summary figure-of-merit), and can then be reported either as additional context added to the trend display of the source physiologic signal, or as their own trended parameter display. For example, in conjunction with displaying an EtCO2 trend on the report, periods of time during which airway leak was present could be denoted on the EtCO2 trend line (via a different line color, style, shading, etc.), thereby alerting the reader/viewer of the report to the fact that the EtCO2 values may be artificially low during those periods of airway leak. The derived parameter could be represented in a binary fashion (e.g., the specific signal feature is either "present" or "not present"), or as a continuous index (representing the amount of the feature present per unit time, and/or the "severity" of whatever amount of the feature that is present). For example, the presence of airway leak could be presented as its own trend line adjacent to the EtCO2 trend. In this embodiment, the ordinate (y-axis) values could represent, for example, the proportion of breath waveforms within the most recent one minute exhibiting an airway leak pattern. Methods of reporting such a derived parameter as additional context added to the trend display of the source physiologic signal include, for example: shading the affected region of the trend display; changing the color or line thickness of the trend data within the affected region; placing indicator markings on or adjacent to the trend display; or adding a text annotation adjacent to the trend display.

6) Since there can sometimes be intervals of missing monitoring data (due to, for example, sensor dislodgement), the affected figures-of-merit could optionally be calculated in a manner that counts the missing data intervals against the figure of merit, or could alternately be calculated in a manner that omits the missing data intervals from the calculation (i.e., only bases the figure-of-merit calculation on intervals with valid data). In either circumstance, the proportion of time in which there is missing data can be reported in conjunction with the affected figure-of-merit.

7) Any of the figures-of-merit representing a "proportion of time" of a specific sub-interval could be additionally or alternately calculated and reported as an "absolute cumulative time".

Additional Example Embodiments of the Post-Event Summary Report

A post-event summary report, automatically generated based on data recorded by a multi-parameter physiologic monitor such as a monitor-defibrillator, from a patient care event that involved positive pressure ventilation, and that depicts trended data from one or more monitored physiologic parameters, including at a minimum trended end-tidal CO2, and that provides a graphical indication (e.g., shading, color, line type, indicator marks, text annotation, etc.) associated with the end-tidal CO2 trend display demarking specific periods of time where the reported end-tidal CO2 values may be erroneously low due to patterns associated with one or more of: airway leak, non-plateauing waveforms, chest compressions, or spontaneous respiratory activity—such patterns being automatically detected by an algorithm in the post-event software, in the monitor that recorded the data, or in an intermediate computing location such as a cloud server;

A post-event summary report, automatically generated based on data recorded by a multi-parameter physiologic monitor such as a monitor-defibrillator, from a patient care event that involved positive pressure ventilation, that depicts trended data from one or more monitored physiologic parameters, including (at a minimum) trended breathing (respiratory/ventilation) rate, and that provides a graphical indication (e.g., shading, color, line type, indicator marks, text annotation, etc.) associated with the breathing rate trend display demarking specific periods of time where the reported breathing rate values may overestimate the true rate of positive pressure ventilation being provided to the patient due to patterns associated with spontaneous respiratory activity—such patterns automatically detected by an algorithm in the post-event software, in the monitor that recorded the data, or in an intermediate computing location such as a cloud server;

A post-event summary report, automatically generated based on data recorded by a multi-parameter physiologic monitor such as a monitor-defibrillator, from a patient care event that involved positive pressure ventilation, that depicts trended data from one or more monitored physiologic parameters, including at a minimum trended breathing (respiratory/ventilation) rate, that displays, simultaneously (e.g., superimposed on each other, or adjacent to each other), breathing rate trend data as derived from at least two different physiologic signals—for example CO2 waveform and airway pressure—or at least two different algorithms processing the same physiologic signal—for example "strict" and "tolerant" breath detection algorithms applied to the CO2 waveform, the "strict" algorithm measuring potentially lower breathing rates than the "tolerant" algorithm due to being designed to preferentially trigger on just positive pressure breaths and ignore breaths that are likely due to patient spontaneous respiratory activity;
  a. the embodiment above, wherein the report graphically calls attention to periods of time when the two breathing rate trends diverge, such divergence potentially being indicative of the presence of patient spontaneous respiratory activity during that interval;

A post-event summary report, automatically generated based on data recorded by a multi-parameter monitor-defibrillator system, which depicts end-tidal O2 trend data;
  a. the embodiment above, wherein the report also depicts at least one figure-of-merit derived from the trended end-tidal 02 measurements;
  b. the embodiments above, wherein the report additionally depicts FiO2 (inspired oxygen concentration) data or a derived figure-of-merit;

A post-event summary report, automatically generated based on data recorded by a multi-parameter physiologic monitor such as a monitor-defibrillator, from a patient care event that involved positive pressure ventilation, that graphically summarizes the distribution of breathing rates measured over a monitoring interval via three or more bins, each bin representing the aggregate absolute or percentage time that the breathing rate was measured to be within a discrete range (e.g., via a histogram);

Example Embodiments of FOMs Provided as Feedback to a Monitor-Defibrillator User During a Patient Care Event In some embodiments, the previously described FOMs may be displayed as feedback to a medical provider during a patient care event, including, but not limited to, during the portion of the patient care event associated with an emergency advanced airway management procedure. The FOMs may be displayed as a text and/or graphical indication, either on the monitor-defibrillator itself, or on any real-time communicatively coupled electronic display, such as a documentation or patient care reporting tablet, a smartphone, a display screen on a video laryngoscope, etc. The FOMs may be calculated based upon the currently elapsed portion of the critical sub-interval of the patient care event associated with the emergency advanced airway management process. In this manner, the FOM would be continuously (or regularly, or semi-continuously) recalculated and the display updated as time elapses during the critical sub-interval. Examples of aforementioned FOMs that may be provided as real-time feedback during a patient care event, and examples of actions that may be taken by the medical provider in response to the FOM feedback, include:

a. The aforementioned "ventilation abnormality indicator" or "ventilation abnormality index" could be provided as a real-time status indicator and/or index value on the display of the monitor-defibrillator (or other communicatively coupled display). This indicator/index could be provided either as a single aggregate FOM (factoring in contributions from each of the one or more constituent $CO_2$ waveform features being reflected by the FOM (i.e., 1: spontaneous respiratory activity in a patient being provided positive pressure ventilation, 2: airway leak, and 3: non-plateauing breath waveforms), and/or as FOMs specific to one or more of the three underlying $CO_2$ waveform features (listed above) being measured. As an "indicator", this FOM could provide a text or graphical indication when the amount of "ventilation abnormality" exceeds a pre-configured threshold, and as an "index", this FOM could provide a text or graphical indication of the amount of "ventilation abnormality" present in the elapsed portion of the critical sub-interval. Here "ventilation abnormality" refers to the amount of spontaneous respiratory activity, airway leak, or non-plateauing breath waveforms, either singly or in combination, present in the $CO_2$ waveform. Such waveform features are well known to those skilled in the art of capnography.

In the context of an emergency airway management process (and specifically the positive-pressure ventilation initiated promptly after the step of successful placement of an airway), the presence of such features provides specific and important insight into the status of the patient and/or the quality with which patient is being managed. Spontaneous respiratory activity during positive pressure ventilation could indicate that a patient requires administration of additional medication, such as a sedative and/or analgesic. In the context of an RSI (or other advanced airway management process involving administration of a paralytic agent), spontaneous respiratory activity indicates that the paralytic effect is wearing off. Knowledge of this development can thus serve, for example, as a valuable passage-of-time indicator for the medical provider, and may represent an indication for administration of additional medication. Airway leak indicates that the breathing circuit or system is not fully "closed", and the effectiveness of ventilation may be compromised by gasses lost through the leak. Knowledge of the presence of a leak would allow the medical provider to assess the airway equipment and breathing system to find and fix the leak, thereby eliminating a potential cause of ineffective ventilation, and thus enhancing the safety and efficacy of the care they are providing the patient. Most importantly, all of the described features represent a situation where the EtCO2 value measured by and displayed on the monitor-defibrillator may be inaccurately low—a critical situation which if not recognized and accounted for, could lead a medical provider to make incorrect patient care decisions, and provide (or with-hold) treatments (e.g. medications, or a specific degree of ventilation) that risk harming the patient.

The "amount" of each of these features present in the $CO_2$ waveform could be measured and quantified as an incidence or density over time (e.g. how many of the breath waveforms over the current elapsed interval exhibit the abnormal feature). In one embodiment, the "amount" of each of these features present in the $CO_2$ waveform could be measured and quantified as a severity (e.g. an average severity across all pertinent breath waveforms) of the abnormality (e.g., for a given exhalation breath waveform in the $CO_2$ signal, an "area under the curve" between the actual phase III of a breath waveform—also known as the alveolar plateau—and a line extrapolating the course of the plateau if it had not been afflicted with the abnormal feature). In other embodiments, the "amount" of each of these features could be measured and quantified as some combination of the incidence/density over time, and the severity of the abnormality. In yet other embodiments, the ventilation abnormality indicator or index could be measured based on a fixed-duration moving time window (e.g., the most recent 2 minutes) within the critical sub-interval of the patient care event associated with the emergency advanced airway management process. A medical provider being provided with this ventilation abnormality indicator or index would thus have access to real-time insight into aspects of the ongoing airway management/ventilation process that are of potentially critical significance to the quality and/or safety of patient care, and that are not reflected in the standard vital signs (e.g. HR, SpO2, RR, EtCO2, blood pressure).

b. The aforementioned "hypoxemia dose index" could be provided as a real-time status indicator and/or index value on the display of the monitor-defibrillator (or other communicatively coupled display). The index may, for example, be calculated based upon the currently elapsed portion of a critical sub-interval of the patient care event associated with the emergency advanced airway management process. This critical sub-interval may for example be the interval between the time of induction of anesthesia, and the time of successful placement of an advanced airway. The time of induction of anesthesia (which for an RSI procedure, is the time at which a paralytic agent is administered to the patient, rendering the patient unable to spontaneously breath) represents the time point at which the patient's oxygen reserves (which are established by the patient's baseline level of oxygen reserve in their blood and lungs, supplemented by whatever amount of pre-oxygenation was provided by the medical provider) begin to be rapidly consumed (since typically no additional oxygen is being actively delivered to the patient's lungs during this sub-interval).

It is well known from the clinical literature that oxygen desaturation (i.e., development of acute hypoxemia) is common during this critical interval of an emergency advanced airway management procedure, and it is also well known that medical providers commonly are unaware of the desaturation as it is happening. Even when providers are aware that a desaturation is occurring (or has occurred), they frequently remain unaware of clues to a worsening severity of the event (such as changes in Heart Rate or characteristics of the ECG), and they also may not appreciate the additive hazard of a concomitant physiologic insult, such as hypotension. Thus a hypoxemia dose index could be provided to a medical provider during an emergency advanced airway management procedure, providing them with significantly enhanced insight into the presence, severity and evolution of a common and commonly underappreciated physiologic hazard during such procedures. Based upon this hypoxemia dose index FOM, the provider may then take important actions that can impact patient morbidity or mortality, such as termination of a laryngoscopy attempt, or progression to a "failed airway" back-up plan (such as use of a different airway device, or an attempt at a surgical airway).

Embodiments of the disclosure, however, are not limited to determining FOMs for a portion of patient care event associated with an emergency advanced airway management procedure, and may be used to indicate to a user a physiological trend data, such as RR or EtCO2, may be erroneous due to artifacts located a CO2 waveform or measured CO2 content during other emergency procedures, such as a cardiac arrest when chest compressions may be provided on a patient. As mentioned above, artifacts caused by various patient, treatment, or equipment factors can alter the shape and/or characteristics of the measured CO2 content to such a degree that both an EtCO2 measurement and a RR measurement are erroneous.

Similar to embodiments discussed above for determining FOMs for the portion of patient care event associated with an emergency advanced airway management procedure, the FOMs other than those associated with an emergency advanced airway management procedure may be provided or generated in post-event review data, or may be provided in real-time or near real-time as feedback during patient care.

As briefly mentioned above, one type of artifact that may be generated in a CO2 waveform is chest compression induced oscillations. These oscillations are a result of small in-and-out movements of the air column in the airway, synchronous with chest compressions. The presence and magnitude of the chest compression induced oscillations can vary substantially between different resuscitation events, as well as over time in a single resuscitation event. It may be beneficial for a medical provider to have information related to the presence and/or characteristics of the chest compression induced oscillations. As such, some embodiments of the disclosure can generate an indication when the chest compression induced oscillations have occurred. Further embodiments can also provide information about the chest compression induced oscillations.

Figure 5:
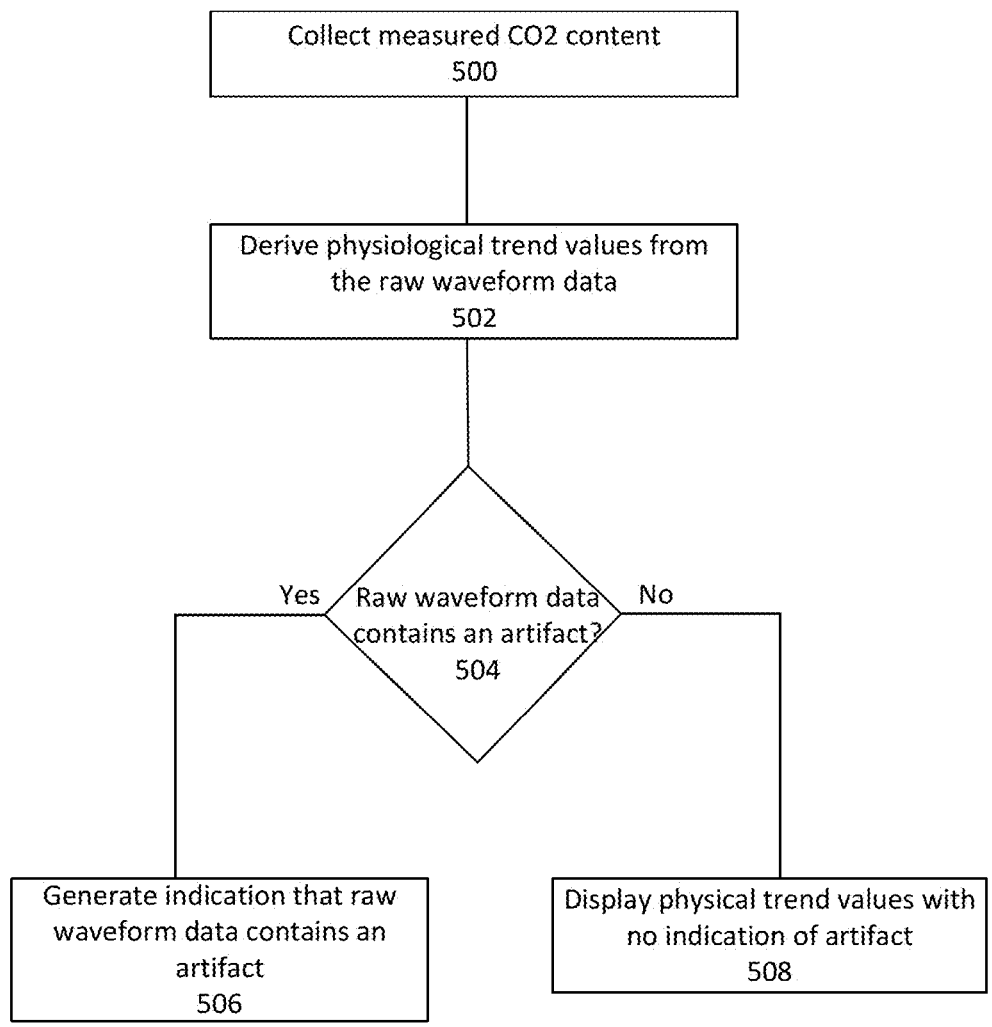
FIG. 5 is a flow chart illustrating one or more processes, methods, functions, or operations that may be performed in implementing an embodiment of the systems and methods described herein.

FIG. 5 illustrates an example of determining whether a CO2 waveform or content contains an artifact, such as a chest compression induced oscillation. As discussed above with reference to FIGS. 2(b) and 2(c), "raw" physiologic waveforms, such as CO2 waveforms, can be collected in operation 500. In operation 502, physiologic trend values, such as EtCO2 or RR, may be derived from the "raw" or measured CO2 content.

Operation 504 determines whether the measured CO2 waveform or content contains an artifact, such as oscillations induced by chest compressions during CPR, or any other type of artifact discussed above. That is, similar to that discussed above with respect to FIG. 2(c), the "raw" measured CO2 content can be "qualified." The artifacts may be identified using any known method. For example, to determine chest compression oscillations, a gating waveform can be used to detect the expected frequency content of chest compressions, such as greater than 100/min or 1.67 Hz), looking for alternating positive/negative slopes above a threshold steepness and/or below a threshold amplitude, and requiring a threshold degree of regularity/periodicity of the candidate features to be designated as a chest compression oscillation. However, embodiments of the disclosure are not limited to determining chest compression induced oscillations in this manner and any known signal processing technique may be used to identify the chest compression induced oscillations. Operations 502 and 504 may be performed simultaneously in some embodiments or operation 504 may be performed prior to operation 502.

If it is determined in operation 504 that artifacts are present in the CO2 waveform or measured content, then an indication can be generated in operation 506 to alert a medical provider that there was an artifact present when the physiological trend values were calculated. The indication can alert the medical provider that the physical trend value calculated when the artifacts are present may not be accurate. That is, the indication can alert the likelihood that the physical trend value is inaccurate. The indication may be any type of alert presented to a user, such as, but not limited to, a text box displayed on the screen of the medical device, changing the color of the displayed physical trend value, an audio alert, or highlighting a portion of a measured CO2 content to indicate where the artifact was present.

For example, the indication may be a text box either displayed on the screen of the medical device and/or included on a FOM in a post-event review that states that an artifact was present during the measurement of the physical trend value. In other embodiments, the physical trend value may be display in one color, such as green, when the value is accurate within a tolerated percentage and may be displayed in another color, such as red or orange, when an artifact is determined to be present so that a medical provider or other user reviewing the post-event report can easily discern which values are accurate and which may be inaccurate due to the artifacts.

Figure 6:
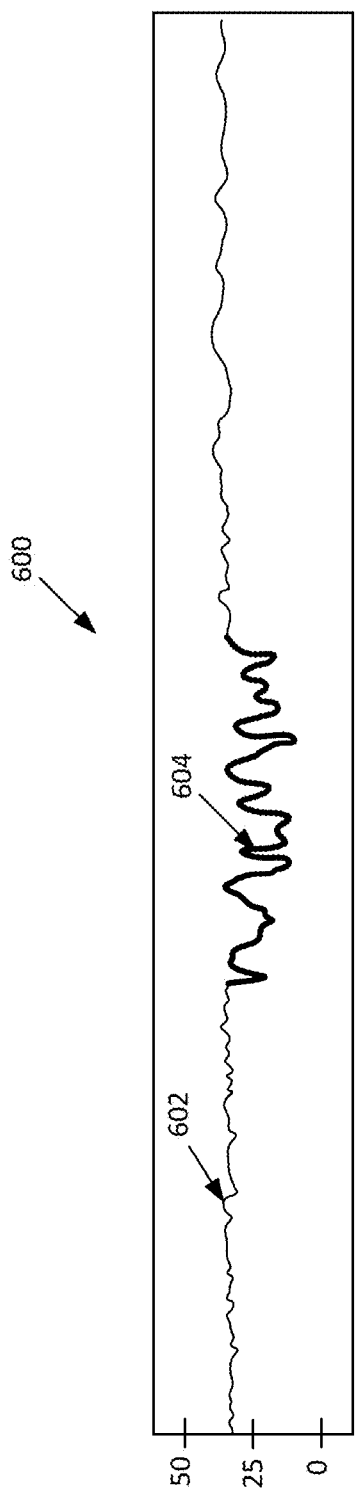
FIG. 6 is an example of a graphical representation of a physical trend value measured according to embodiments of the disclosure.

In other embodiments, the actual measured CO2 content or physical trend value may be alerted so that any portion that contains artifacts is highlighted to a user, such as changing the color of the content or creating a bold line when the content has an artifact. FIG. 6 illustrates one such an indication that measured physical trend values are inaccurate or unreliable. That is, an indication that the measured physical trend value does not accurately reflect the value that would have been measured if the artifact was not present. FIG. 6 shows an example of a measured EtCO2 value 600 during a resuscitation event. The portion of the EtCO2 value that was measured from CO2 content that did not have chest compressed induced oscillations is shown with a thinner line 602. The portion of the EtCO2 value that was measured when artifacts were present in the measured CO2 content is shown with a thicker line 604. This can allow a user looking at the data to quickly discern which data is reliable.

Embodiments of the disclosure, however, are not limited to these examples of indications that may be generated to alert a user that the measured CO2 content contains an artifact and any indication that allows a user to see that an artifact is present may be used.

In some embodiments, it may be determined whether an artifact present in the measured CO2 contents violates a predetermined threshold. If the artifact does not violate a predetermined threshold, then the physical trend value derived may not be effected or may be effected within a tolerated range. In such embodiments, operation 504 will determine no artifact is present since it does not violate a predetermined threshold and the physical trend value is accurate within a tolerated range. The threshold may be stored in a memory of the device and/or may be set by a user.

In some embodiments, the indication generated in operation 504 may be not including particular physical trend values, such as EtCO2 or RR measurements, in post-event review data when it is determined that there are artifacts in the measured CO2 content and therefore the physical trend values are not accurate.

If it is determined in operation 504 that the measured CO2 content does not contain any artifacts and/or the artifacts do not violate a predetermined threshold, then the physical trend data may be displayed in operation 508 without any indication of the artifacts.

The example illustrated in FIG. 5 can be performed either during post-event review or may be performed in real-time or near-real-time (such as with a latency of less than 2 minutes) during a patient care event and displayed directly on a display of a medical device or another type of display, such as, but not limited to, a smart phone or tablet, connected to the medical device.

In addition to displaying the indication that artifacts are present, if the artifact is a chest compression induced oscillation, some embodiments of the disclosure can measure or determine various characteristics of the oscillation. For example, in some embodiments, a magnitude of each chest compression oscillation, if present, can be determined. The determined magnitude can be displayed as a numerical value along with either the measured CO2 content and/or the physical trend value.

Oscillations typically appear as transient dips in an otherwise flat or upsloping phase 3 (exhalation plateau) of a capnogram. The dips can be of variable depth, infrequently extending all the way down to the waveform baseline. The dips also may or may not return to the pre-dip maximum value before a next dip begins. Each of these characteristics can be measured by known signal processing techniques.

The magnitude of each oscillation can be expressed as the absolute depth of the oscillation (e.g., the maximum minus minimum CO2 partial pressure measurement associated with each dip) or as the relative depth (e.g., maximum minus minimum CO2 partial pressure measurement associated with each dip, divided by a current EtCO2 value).

The magnitude of each oscillation may be summarized within a certain time interval. For example, oscillation magnitude within a certain time interval, such as one breath cycle or alternatively one minute, etc., could be expressed as the maximum single oscillation magnitude within that interval, or as the mean or median of all oscillations within that interval, etc.

In addition to or alternatively to the magnitude, it can be determined the proportion of each respiratory/ventilation cycle over which the chest compression induced oscillation occurs. A respiratory/ventilation cycle is the interval between the beginning of one breath event and the beginning of the next breath event. The term "respiration" is commonly used when a breath is a spontaneous inspiration and expiration occurring due to the respiratory efforts, whether conscious and intentional or sub-conscious and automatically driven, of the patient. The term "ventilation" is commonly used when a breath is delivered via positive-pressure by an external source, such as mechanical ventilator or a medical provider manually squeezing a ventilation bag. Embodiments of the disclosure are not limited to the type of breath source and only requires that breathing is occurring. Therefore, respiratory/ventilation cycle refers to the period of one breath, regardless of who or what caused the breath to occur.

The proportion of the respiratory/ventilation cycle over which the chest compression induced oscillations occur can be measured and quantified in various ways. For example, within one breath cycle, the interval between the beginning of the first chest compression induced oscillation and the end of the last chest compression induced oscillation can be divided by the duration of the breath cycle. In another example, the cumulative duration of all chest compression induced oscillations with an arbitrary, pre-defined, or user-configured time interval can be divided by the total duration of the time interval.

In addition or alternatively to the magnitude and proportion, a "burden" of chest compression induced oscillations over a certain time interval can be determined. As one example, this "burden" can be measured as the proportion of the total interval during which chest compression induced oscillations are present. In this example, the burden is essentially equivalent to, for a given breath cycle, the proportion of the breath cycle over which chest compression induced oscillations occurred.

The "burden," however, can be determine in other ways as well. For example, each chest compression induced oscillation can be required to have a threshold magnitude to be considered part of the "burden." As another example, each breath cycle can be required to have a threshold proportion of the breath cycle over which the oscillations are occurring to contribute to the "burden." And as yet another example, both the magnitude and threshold considerations can be combined to determine the "burden." That is, chest compression induced oscillations may only be considered if they are above a threshold magnitude and occur during a threshold proportion of the breath cycle or, alternatively, chest compression induced oscillations may only be considered as part of the "burden" if they are either above the threshold magnitude or occur during a threshold proportion of the breath cycle.

Rather than just being measured over a predetermined period of time, in some embodiments the "burden" may be determined over an entire measured CO2 waveform or content. Further, in some embodiments, the "burden" may be determined over shorter, fixed, or user-configurable intervals. For example, the "burden" could be determined before and then after a change in treatment of patient conditions, which could provide useful feedback on the impact of that treatment or condition change on that patient's airway status.

Since excessive chest compression induced oscillations can interfere with normal phase three (expiratory plateau) of the capnogram, they can also increase the difference between alveolar CO2 levels and EtCO2 measurements. And since EtCO2 measurements are used as a proxy for alveolar CO2 levels, progressively more severe chest compression induced oscillations can cause a progressively more severe underestimation of the physiological value that medical providers are employing capnography to assess. Therefore, the presence or burden of chest compression induced oscillations can also be used to alert a user or medical provider, such as by the indication discussed above, of the fact that the EtCO2 measurement may be artificially lower than it otherwise would be, due to the effect of the chest compression induced oscillations on phase three of the capnogram.

The "burden" can not only be a proportion, as described above, but also as an index depicted numerically or graphically on an arbitrary scale, such as 0 to 10, with 0 representing complete absence of chest compression induced oscillations and 10 representing the presence of chest compression induced oscillations through the measured time interval.

Additionally or alternatively, other time-based measurements or determinations may be useful to describe and summarize the chest compression induced oscillations in the measured CO2 content. For example, for any given point in time, the elapsed duration for which chest compression induced oscillations have been present (or, alternatively, have been absent) can be determined and displayed.

All of the above-discussed measurements for chest compression induced oscillations can be useful and valuable in either a post-event quality-of-care or quality improvement report, as well as in real-time or near real-time. For both the post-event and real, or near real-time monitoring use, the measurements discussed above could be presented as periodic measurements, such as updated every 30 seconds, or as a continuous trend, such as being updated every second or every breath event.

In some embodiments, the measured CO2 content may be continuously displayed on the medical device to a user or medical provider. When artifacts are found to be present in the measured CO2 content, the portion of the measured CO2 content that has the artifact may be highlighted in some manner to alert that the data in that measured CO2 content may not be accurate. Further, in some embodiments, the one or more physiological trend values may be displayed time-aligned with the measured CO2 content. This can allow a user to quickly see which physiological trend values may not be accurate if they align with a portion of the measured CO2 content that is highlight as containing an artifact.

In a post-event record of a patient care event, such as a quality-of-care report, or quality improvement report, an indication may be included with the data that the measured CO2 content was derived during a cardiac arrest which required the use of chest compressions. The post-event report can then indicate what physical trend values may not be accurate due to the chest compressions induced oscillations in the measured CO2 data. In some embodiments, the post-event report may not include any physical trend values that occurred during chest compression induced oscillations and are determined not to be accurate.

In some embodiments, when a medical device determines that an artifact is present and that the physical trend value measured may be unreliable based on the artifacts, EtCO2 alarms, alerts, or decision-support operations can be either adjusted or disabled. In some embodiments, the alarms, alerts, or decision-support operations may only be disabled if the artifacts present in the measured CO2 content violate a predetermined threshold, which may be predetermined and stored in memory of the medical device, or may be configured by a user through a user interface of the medical device.

Figure 7:
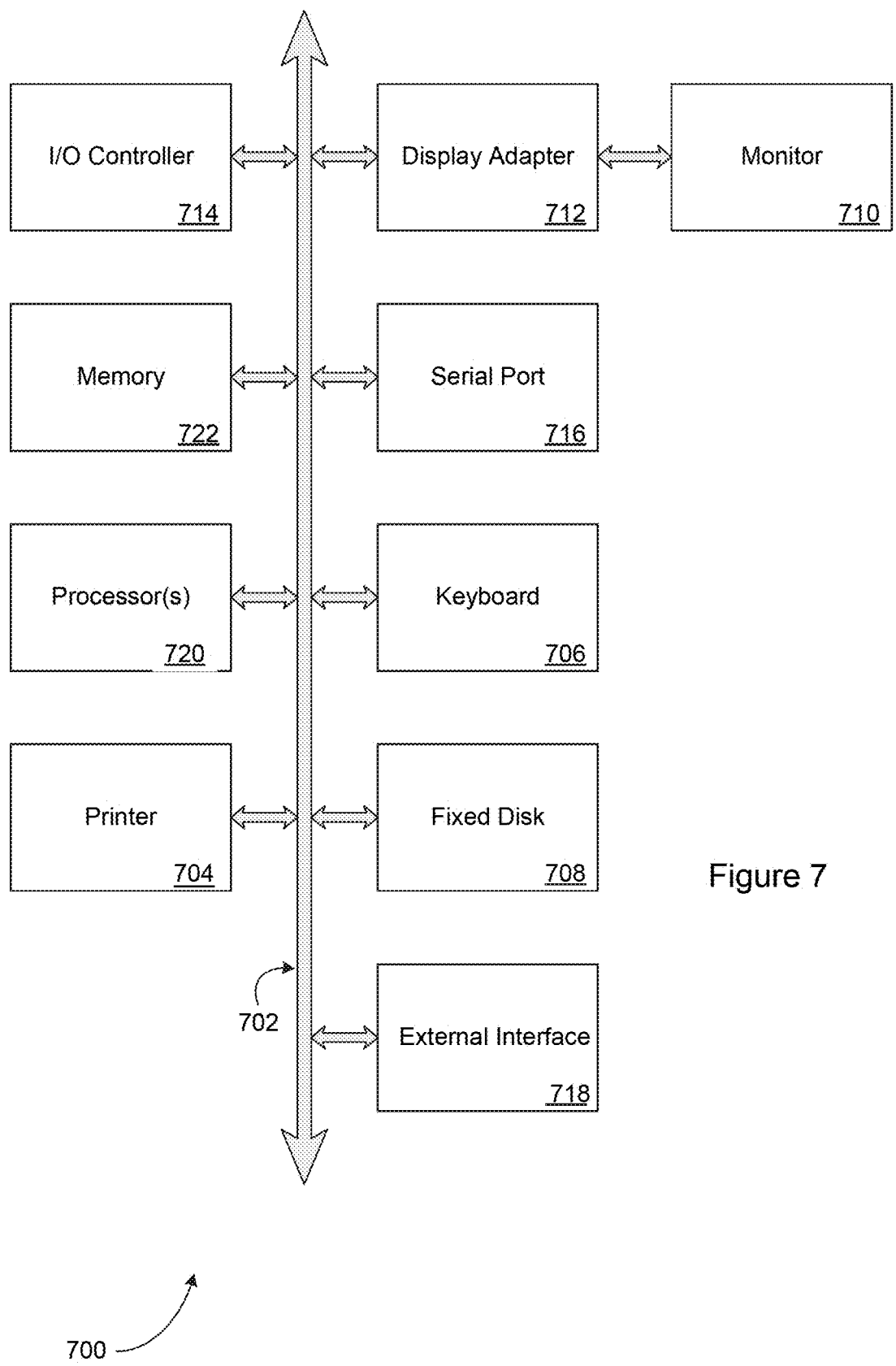
FIG. 7 is a diagram illustrating elements or components that may be present in a computer device or system configured to implement a method, process, function, or operation in accordance with an embodiment of the disclosure.

FIG. 7 is a diagram illustrating elements or components that may be present in a computer device or system configured to implement a method, process, function, or operation in accordance with an embodiment of the disclosure. The elements or components of FIG. 7 may be included, for example, in a medical device and/or a post-event review device. As noted, in some embodiments, the system and methods described herein may be implemented in the form of an apparatus that includes a processing element and set of executable instructions. The executable instructions may be part of a software application and arranged into a software architecture. In general, an embodiment of the disclosure may be implemented using a set of software instructions that are designed to be executed by a suitably programmed processing element (such as a CPU, microprocessor, processor, controller, computing device, etc.). In a complex application or system such instructions are typically arranged into "modules" with each such module typically performing a specific task, process, function, or operation. The entire set of modules may be controlled or coordinated in their operation by an operating system (OS) or other form of organizational platform.

Each application module or sub-module may correspond to a particular function, method, process, or operation that is implemented by the module or sub-module. Such function, method, process, or operation may include those used to implement one or more aspects of the system and methods described herein.

The application modules and/or sub-modules may include any suitable computer-executable code or set of instructions (e.g., as would be executed by a suitably programmed processor, microprocessor, or CPU), such as computer-executable code corresponding to a programming language. For example, programming language source code may be compiled into computer-executable code. Alternatively, or in addition, the programming language may be an interpreted programming language such as a scripting language. The computer-executable code or set of instructions may be stored in (or on) any suitable non-transitory computer-readable medium. In general, with regards to the embodiments described herein, a non-transitory computer-readable medium may include almost any structure, technology or method apart from a transitory waveform or similar medium.

As described, the system, apparatus, methods, processes, functions, and/or operations for implementing an embodiment of the disclosure may be wholly or partially implemented in the form of a set of instructions executed by one or more programmed computer processors such as a central processing unit (CPU) or microprocessor. Such processors may be incorporated in an apparatus, server, client or other computing or data processing device operated by, or in communication with, other components of the system. As an example, FIG. 7 is a diagram illustrating elements or components that may be present in a computer device or system 700 configured to implement a method, process, function, or operation in accordance with an embodiment of the disclosure. The subsystems shown in FIG. 7 are interconnected via a system bus 702. Additional subsystems include a printer 704, a keyboard 706, a fixed disk 708, and a monitor 710, which is coupled to a display adapter 712. Peripherals and input/output (I/O) devices, which couple to an I/O controller 714, can be connected to the computer system by any number of means known in the art, such as a serial port 716. For example, the serial port 716 or an external interface 718 can be utilized to connect the computer device 700 to further devices and/or systems not shown in FIG. 7 including a wide area network such as the Internet, a mouse input device, and/or a scanner. The interconnection via the system bus 702 allows one or more processors 720 to communicate with each subsystem and to control the execution of instructions that may be stored in a system memory 722 and/or the fixed disk 708, as well as the exchange of information between subsystems. The system memory 722 and/or the fixed disk 708 may embody a tangible computer-readable medium.

Any of the software components, processes or functions described in this application may be implemented as software code to be executed by a processor using any suitable computer language such as, for example, Java, JavaScript, C++ or Perl using, for example, conventional or object-oriented techniques. The software code may be stored as a series of instructions, or commands in (or on) a non-transitory computer-readable medium, such as a random-access memory (RAM), a read only memory (ROM), a magnetic medium such as a hard-drive or a floppy disk, or an optical medium such as a CD-ROM. In this context, a non-transitory computer-readable medium is almost any medium suitable for the storage of data or an instruction set, aside from a transitory waveform. Any such computer readable medium may reside on or within a single computational apparatus, and may be present on or within different computational apparatuses within a system or network.

According to one example implementation, the term processing element or processor, as used herein, may be a central processing unit (CPU), or conceptualized as a CPU (such as a virtual machine). In this example implementation, the CPU or a device in which the CPU is incorporated may be coupled, connected, and/or in communication with one or more peripheral devices, such as display.

The non-transitory computer-readable storage medium referred to herein may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, synchronous dynamic random access memory (SDRAM), or similar devices or other forms of memories based on similar technologies. As mentioned, with regards to the embodiments described herein, a non-transitory computer-readable medium may include almost any structure, technology or method apart from a transitory waveform or similar medium.

Certain implementations of the disclosed technology are described herein with reference to block diagrams of systems, and/or to flowcharts or flow diagrams of functions, operations, processes, or methods. It will be understood that one or more blocks of the block diagrams, or one or more stages or steps of the flowcharts or flow diagrams, and combinations of blocks in the block diagrams and stages or steps of the flowcharts or flow diagrams, respectively, can be implemented by computer-executable program instructions. Note that in some embodiments, one or more of the blocks, or stages or steps may not necessarily need to be performed in the order presented, or may not necessarily need to be performed at all.

These computer-executable program instructions may be loaded onto a general-purpose computer, a special purpose computer, a processor, or other programmable data processing apparatus to produce a specific example of a machine, such that the instructions that are executed by the computer, processor, or other programmable data processing apparatus create means for implementing one or more of the functions, operations, processes, or methods described herein. These computer program instructions may also be stored in a computer-readable memory that can direct a computer or other programmable data processing apparatus to function in a specific manner, such that the instructions stored in the computer-readable memory produce an article of manufacture including instruction means that implement one or more of the functions, operations, processes, or methods described herein.

While certain implementations of the disclosed technology have been described in connection with what is presently considered to be the most practical and various implementations, it is to be understood that the disclosed technology is not to be limited to the disclosed implementations. Instead, the disclosed implementations are intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural and/or functional elements that do not differ from the literal language of the claims, or if they include structural and/or functional elements with insubstantial differences from the literal language of the claims.

The subject matter of the embodiments described herein are described with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

That which is claimed is:

1. A device for evaluating measured carbon dioxide ($CO_2$) content in an exhaled breath, comprising:
an input configured to receive the measured $CO_2$ content;
a user interface; and
a processor configured to:
generate a measurement based on the measured $CO_2$ content;
identify alternating positive and negative slopes in the measured $CO_2$ content;
determine that the measured $CO_2$ content comprises positive pressure ventilation induced artifacts by:
determining that the alternating positive and negative slopes have greater than a threshold steepness; and
determining that a periodicity of the positive and negative slopes is above a threshold periodicity;
in response to determining that the measured $CO_2$ content comprises the positive pressure ventilation induced artifacts,
determine a likelihood that the measurement is unreliable;
display, on the user interface, a portion of the measurement indicative of artifacts in a first color and a portion of the measurement devoid of artifacts in a second color; and
indicate, on the user interface, the likelihood that the measurement is unreliable.

2. The device of claim 1, wherein the processor is further configured to determine a characteristic of the positive pressure ventilation induced artifacts and the user interface is configured to indicate the characteristic.

3. The device of claim 1, wherein the measurement comprises an end tidal $CO_2$ value or a respiratory rate.

4. A device for evaluating measured carbon dioxide ($CO_2$) content in an exhaled breath, comprising:
an input configured to receive the measured $CO_2$ content;
a user interface; and
a processor configured to:
generate a measurement based on the measured $CO_2$ content;
identify alternating positive and negative slopes in the measured $CO_2$ content;
determine that the measured $CO_2$ content comprises positive pressure ventilation induced artifacts by:

determining that the alternating positive and negative slopes have greater than a threshold steepness; and determining that a periodicity of the positive and negative slopes is above a threshold periodicity;

in response to determining that the measured $CO_2$ content comprises positive pressure ventilation induced artifacts, determine a likelihood that the measurement is unreliable;

highlight, on the user interface, a portion of the measurement indicative of the positive pressure ventilation induced artifacts; and indicate, on the user interface, the likelihood the measurement is unreliable.

5. The device of claim 4, wherein the processor is further configured to determine a characteristic of the positive pressure ventilation induced artifacts and the user interface is configured to indicate the characteristic.

6. The device of claim 5, wherein the characteristic comprises a timing of the positive pressure ventilation induced artifacts.

7. The device of claim 5, wherein the characteristic comprises a proportion of a total interval in which the positive pressure ventilation induced artifacts are present.

8. The device of claim 7, wherein the processor is configured to determine that the measured $CO_2$ content comprises the positive pressure ventilation induced artifacts by determining that a magnitude of the positive pressure ventilation induced artifacts in the total interval is equal to or greater than a threshold.

9. The device of claim 8, wherein the device is a monitor-defibrillator or a post-event review device.

10. A method for evaluating measured carbon dioxide ($CO_2$) content in an exhaled breath, the method comprising:
receiving the measured $CO_2$ content;
identify alternating positive and negative slopes in the measured $CO_2$ content;
determining, by a processor, that the measured $CO_2$ content comprises artifacts by:
determining that the alternating positive and negative slopes have greater than a threshold steepness; and
determining that a periodicity of the positive and negative slopes is above a threshold periodicity, the artifacts comprising ventilation induced artifacts;

in response to determining that the measured $CO_2$ content comprises the artifacts, determining, by the processor, a likelihood that the measured CO2 content is unreliable;

displaying, by a user interface, a portion of the measured $CO_2$ content indicative of the artifacts in a first color and a portion of the measured $CO_2$ content devoid of artifacts in a second color; and indicating, by the user interface, the likelihood that the measured $CO_2$ content is unreliable.

11. The method of claim 10, further comprising:
generating a measurement based on the measured $CO_2$ content; and
indicating a likelihood that the measurement is unreliable when the measured $CO_2$ content includes the artifacts.

12. The method of claim 11, wherein the measurement comprises an end tidal $CO_2$ value or a respiratory rate.

13. The method of claim 11, further comprising concurrently displaying, on a display, the measurement and the likelihood the measurement is unreliable.

14. The device of claim 1, wherein the processor is configured to:
determine the likelihood that the measurement is unreliable by comparing a magnitude of the artifacts to a threshold.

15. The device of claim 14, wherein the processor is further configured to:
determine that the artifacts comprise chest compression induced artifacts; and
in response to determining that the artifacts comprise chest compression induced artifacts, determine a magnitude of the chest compression induced artifacts; and
wherein the user interface is further configured to indicate the magnitude of the chest compression induced artifacts.

16. The device of claim 1, further comprising a $CO_2$ sensor configured to measure the $CO_2$ content.

17. The method of claim 12, further comprising:
determining a magnitude of the artifacts; and
displaying, by the user interface, the magnitude of the artifacts.

18. The device of claim 1, wherein the processor is further configured to:
disable an end-tidal $CO_2$ alarm in response to determining the likelihood that the measurement is unreliable.

* * * * *